(12) United States Patent
Felt et al.

(10) Patent No.: US 9,510,953 B2
(45) Date of Patent: Dec. 6, 2016

(54) MODULAR SEGMENTED DISC NUCLEUS IMPLANT

(71) Applicant: Vertebral Technologies, Inc. (VTI), Minnetonka, MN (US)

(72) Inventors: Jeffrey C. Felt, Greenwood, MN (US); Mark A. Rydell, Golden Valley, MN (US); Stephen H. Crosbie, Prior Lake, MN (US); John P. Mehawej, Robbinsdale, MN (US)

(73) Assignee: Vertebral Technologies, Inc., Minnetonka, MN (US)

( * ) Notice: Subject to any disclaimer, the term of this patent is extended or adjusted under 35 U.S.C. 154(b) by 25 days.

(21) Appl. No.: 13/833,998

(22) Filed: Mar. 15, 2013

(65) Prior Publication Data
US 2013/0245770 A1    Sep. 19, 2013

Related U.S. Application Data

(60) Provisional application No. 61/685,383, filed on Mar. 16, 2012.

(51) Int. Cl.
| | | |
|---|---|---|
| *A61F 2/44* | (2006.01) | |
| *A61F 2/46* | (2006.01) | |
| *A61F 2/30* | (2006.01) | |

(52) U.S. Cl.
CPC .............. *A61F 2/442* (2013.01); *A61F 2/4611* (2013.01); *A61F 2002/305* (2013.01);
(Continued)

(58) Field of Classification Search
CPC ... A61B 17/1757; A61B 17/7074; A61F 2/44; A61F 2/442; A61F 2/444
(Continued)

(56) References Cited

U.S. PATENT DOCUMENTS

| | | |
|---|---|---|
| 3,030,951 A | 4/1962 | Mandarino |
| 3,728,742 A | 4/1973 | Averill et al. |

(Continued)

FOREIGN PATENT DOCUMENTS

| | | |
|---|---|---|
| CN | 101193608 | 6/2008 |
| DE | 43 39 895 | 3/1995 |

(Continued)

OTHER PUBLICATIONS

Search Report dated Nov. 11, 2015 for EP Application No. 13761691.8, 7 pages.
(Continued)

*Primary Examiner* — Matthew Lawson
(74) *Attorney, Agent, or Firm* — Patterson Thuente Pedersen, P.A.

(57) ABSTRACT

A segmented disc nucleus replacement prosthesis and system for its implantation wherein the segments are made of a compliant, homogeneous material throughout. The prosthesis comprises a plurality of modular segments that mate together in a rail-and-slot arrangement. The rails and slots are configured to interlock and hold together under load despite being formed of compliant materials. In one embodiment, insertion tools and stabilizers are utilized for manipulation of the modular segments, the insertion tools and stabilizers being designed to accommodate for handling the compliant modular segments.

10 Claims, 10 Drawing Sheets

(52) U.S. Cl.
CPC ............... *A61F 2002/30069* (2013.01); *A61F 2002/30387* (2013.01); *A61F 2002/30604* (2013.01); *A61F 2002/444* (2013.01); *A61F 2002/4687* (2013.01)

(58) Field of Classification Search
USPC .......................................... 623/17.11–17.16
See application file for complete search history.

(56) References Cited

U.S. PATENT DOCUMENTS

| | | |
|---|---|---|
| 3,815,599 A | 6/1974 | Deyerle |
| 3,848,601 A | 11/1974 | Ma et al. |
| 3,867,728 A | 2/1975 | Stubstad et al. |
| 3,867,729 A | 2/1975 | Stubstad et al. |
| 4,081,866 A | 4/1978 | Upshaw et al. |
| 4,203,444 A | 5/1980 | Bonnell et al. |
| 4,349,921 A | 9/1982 | Kuntz |
| 4,456,745 A | 6/1984 | Rajan |
| 4,463,141 A | 7/1984 | Robinson |
| 4,476,293 A | 10/1984 | Robinson |
| 4,477,604 A | 10/1984 | Oechsle, III |
| 4,502,161 A | 3/1985 | Wall |
| 4,647,643 A | 3/1987 | Zdrahala et al. |
| 4,651,736 A | 3/1987 | Sanders |
| 4,711,639 A | 12/1987 | Grundei |
| 4,722,948 A | 2/1988 | Sanderson |
| 4,743,256 A | 5/1988 | Brantigan |
| 4,743,632 A | 5/1988 | Marinovic |
| 4,772,287 A | 9/1988 | Ray et al. |
| 4,808,691 A | 2/1989 | Konig et al. |
| 4,834,757 A | 5/1989 | Brantigan |
| 4,863,476 A | 9/1989 | Shepperd |
| 4,873,308 A | 10/1989 | Coury et al. |
| 4,880,610 A | 11/1989 | Constantz |
| 4,904,260 A | 2/1990 | Ray et al. |
| 4,911,718 A | 3/1990 | Lee et al. |
| 4,969,888 A | 11/1990 | Scholten et al. |
| 5,007,940 A | 4/1991 | Berg |
| 5,047,055 A | 9/1991 | Bao et al. |
| 5,067,964 A | 11/1991 | Richmond et al. |
| 5,082,803 A | 1/1992 | Sumita |
| 5,108,404 A | 4/1992 | Scholten et al. |
| 5,109,077 A | 4/1992 | Wick |
| 5,143,942 A | 9/1992 | Brown |
| 5,166,115 A | 11/1992 | Brown |
| 5,192,326 A | 3/1993 | Bao et al. |
| 5,192,327 A | 3/1993 | Brantigan |
| 5,254,662 A | 10/1993 | Szycher et al. |
| 5,263,987 A | 11/1993 | Shah |
| 5,278,201 A | 1/1994 | Dunn et al. |
| 5,344,458 A | 9/1994 | Bonutti |
| 5,344,459 A | 9/1994 | Swartz |
| 5,397,364 A | 3/1995 | Kozak et al. |
| 5,458,643 A | 10/1995 | Oka et al. |
| 5,509,934 A | 4/1996 | Cohen |
| 5,514,180 A | 5/1996 | Heggeness |
| 5,522,899 A | 6/1996 | Michelson |
| 5,525,418 A | 6/1996 | Hashimoto et al. |
| 5,545,229 A | 8/1996 | Parsons et al. |
| 5,549,683 A | 8/1996 | Bonutti |
| 5,554,191 A | 9/1996 | Lahille et al. |
| 5,556,429 A | 9/1996 | Felt |
| 5,562,736 A | 10/1996 | Ray et al. |
| 5,609,635 A | 3/1997 | Michelson |
| 5,624,463 A | 4/1997 | Stone et al. |
| 5,674,294 A | 10/1997 | Bainville et al. |
| 5,702,453 A | 12/1997 | Rabbe et al. |
| 5,702,454 A | 12/1997 | Baumgartner |
| 5,725,531 A | 3/1998 | Shapiro |
| 5,755,797 A | 5/1998 | Baumgartner |
| 5,772,661 A | 6/1998 | Michelson |
| 5,776,199 A | 7/1998 | Michelson |
| 5,795,353 A | 8/1998 | Felt |
| 5,800,547 A | 9/1998 | Schafer et al. |
| 5,824,093 A | 10/1998 | Ray et al. |
| 5,860,973 A | 1/1999 | Michelson |
| 5,861,041 A | 1/1999 | Tienboon |
| 5,888,220 A | 3/1999 | Felt et al. |
| 5,888,227 A | 3/1999 | Cottle |
| 5,888,228 A | 3/1999 | Knothe et al. |
| 5,893,889 A | 4/1999 | Harrington |
| 5,919,236 A | 7/1999 | Pfaff et al. |
| 5,944,759 A | 8/1999 | Link |
| 5,980,522 A | 11/1999 | Koros et al. |
| 5,989,289 A | 11/1999 | Coates et al. |
| 5,989,291 A | 11/1999 | Ralph et al. |
| 6,033,438 A | 3/2000 | Bianchi et al. |
| 6,048,345 A | 4/2000 | Berke et al. |
| 6,079,868 A | 6/2000 | Rydell |
| 6,080,193 A | 6/2000 | Hochshuler et al. |
| 6,096,038 A | 8/2000 | Michelson |
| 6,096,080 A | 8/2000 | Nicholson et al. |
| 6,102,950 A | 8/2000 | Vaccaro |
| 6,110,210 A | 8/2000 | Norton et al. |
| 6,113,638 A | 9/2000 | Williams et al. |
| 6,117,174 A | 9/2000 | Nolan |
| 6,132,472 A | 10/2000 | Bonutti |
| 6,139,579 A | 10/2000 | Steffee et al. |
| 6,140,452 A | 10/2000 | Felt et al. |
| 6,143,033 A | 11/2000 | Paul et al. |
| 6,146,422 A | 11/2000 | Lawson |
| 6,159,211 A | 12/2000 | Boriani et al. |
| 6,174,311 B1 | 1/2001 | Branch et al. |
| 6,176,882 B1 | 1/2001 | Biedermann et al. |
| 6,183,517 B1 | 2/2001 | Suddaby |
| 6,190,414 B1 | 2/2001 | Young et al. |
| 6,206,923 B1 | 3/2001 | Boyd et al. |
| 6,206,927 B1 | 3/2001 | Fell et al. |
| 6,224,630 B1 | 5/2001 | Bao et al. |
| 6,224,631 B1 | 5/2001 | Kohrs |
| 6,245,108 B1 | 6/2001 | Biscup |
| 6,248,131 B1 | 6/2001 | Felt et al. |
| 6,251,140 B1 | 6/2001 | Marino et al. |
| 6,258,125 B1 | 7/2001 | Paul et al. |
| 6,264,695 B1 | 7/2001 | Stoy |
| 6,270,528 B1 | 8/2001 | McKay |
| 6,302,914 B1 | 10/2001 | Michelson |
| 6,342,075 B1 | 1/2002 | MacArthur |
| 6,348,071 B1 | 2/2002 | Steffee et al. |
| 6,371,988 B1 | 4/2002 | Pafford et al. |
| 6,371,990 B1 | 4/2002 | Ferree |
| 6,387,130 B1 | 5/2002 | Stone et al. |
| 6,419,704 B1 | 7/2002 | Ferree |
| 6,419,705 B1 | 7/2002 | Erickson |
| 6,436,140 B1 | 8/2002 | Liu et al. |
| 6,436,143 B1 | 8/2002 | Ross et al. |
| 6,440,169 B1 | 8/2002 | Elberg et al. |
| 6,443,988 B2 | 9/2002 | Felt et al. |
| 6,468,311 B2 | 10/2002 | Boyd et al. |
| 6,488,710 B2 | 12/2002 | Besselink |
| 6,511,509 B1 | 1/2003 | Ford et al. |
| 6,524,341 B2 | 2/2003 | Lang et al. |
| 6,533,818 B1 | 3/2003 | Weber et al. |
| 6,537,280 B2 | 3/2003 | Dinger et al. |
| 6,558,421 B1 | 5/2003 | Fell et al. |
| 6,558,424 B2 | 5/2003 | Thalgott |
| 6,562,074 B2 | 5/2003 | Gerbec et al. |
| 6,595,998 B2 | 7/2003 | Johnson et al. |
| 6,610,092 B2 | 8/2003 | Ralph et al. |
| 6,610,093 B1 | 8/2003 | Pisharodi |
| 6,620,196 B1 | 9/2003 | Trieu |
| 6,648,917 B2 | 11/2003 | Gerbec et al. |
| 6,652,587 B2 | 11/2003 | Felt et al. |
| 6,669,732 B2 | 12/2003 | Serhan et al. |
| 6,726,720 B2 | 4/2004 | Ross et al. |
| 6,726,721 B2 | 4/2004 | Stoy et al. |
| 6,733,535 B2 | 5/2004 | Michelson |
| 6,740,093 B2 | 5/2004 | Hochschuler et al. |
| 6,764,514 B1 | 7/2004 | Li et al. |
| 6,770,095 B2 | 8/2004 | Grinberg et al. |
| 6,773,460 B2 | 8/2004 | Jackson |
| 6,793,678 B2 | 9/2004 | Hawkins |
| 6,821,298 B1 | 11/2004 | Jackson |

(56) References Cited

U.S. PATENT DOCUMENTS

| | | |
|---|---|---|
| 6,835,206 B2 | 12/2004 | Jackson |
| 6,852,129 B2 | 2/2005 | Gerbec et al. |
| 6,855,165 B2 | 2/2005 | Fell et al. |
| 6,855,167 B2 | 2/2005 | Shimp et al. |
| 6,866,684 B2 | 3/2005 | Fell et al. |
| 6,893,463 B2 | 5/2005 | Fell et al. |
| 6,896,701 B2 | 5/2005 | Boyd et al. |
| 6,911,044 B2 | 6/2005 | Fell et al. |
| 6,923,831 B2 | 8/2005 | Fell et al. |
| 6,966,928 B2 | 11/2005 | Fell et al. |
| 7,001,431 B2 | 2/2006 | Bao et al. |
| 7,008,452 B2 | 3/2006 | Hawkins |
| 7,018,416 B2 | 3/2006 | Hanson et al. |
| 7,238,204 B2 | 7/2007 | Le Couedic et al. |
| 7,267,690 B2 | 9/2007 | Felt |
| 7,291,171 B2 | 11/2007 | Ferree |
| 7,297,161 B2 | 11/2007 | Fell |
| 7,320,709 B2 | 1/2008 | Felt et al. |
| 7,341,602 B2 | 3/2008 | Fell et al. |
| 7,491,235 B2 | 2/2009 | Fell |
| 7,491,237 B2 | 2/2009 | Randall et al. |
| 7,563,285 B2 | 7/2009 | Ralph et al. |
| 7,591,853 B2 | 9/2009 | Felt et al. |
| 7,618,458 B2 | 11/2009 | Biedermann et al. |
| 7,621,960 B2 | 11/2009 | Boyd et al. |
| 7,666,228 B2 | 2/2010 | Le Couedic et al. |
| 7,914,582 B2 | 3/2011 | Felt et al. |
| 8,038,718 B2 | 10/2011 | Palm et al. |
| 8,100,977 B2 | 1/2012 | Felt |
| 8,828,019 B1 * | 9/2014 | Raymond et al. ............... 606/99 |
| 2001/0004710 A1 | 6/2001 | Felt et al. |
| 2001/0047207 A1 | 11/2001 | Michelson |
| 2002/0026244 A1 | 2/2002 | Trieu |
| 2002/0029084 A1 | 3/2002 | Paul et al. |
| 2002/0099444 A1 | 7/2002 | Boyd et al. |
| 2002/0127264 A1 | 9/2002 | Felt et al. |
| 2002/0128713 A1 | 9/2002 | Ferree |
| 2002/0183850 A1 | 12/2002 | Felt et al. |
| 2003/0055506 A1 | 3/2003 | Stoy et al. |
| 2003/0065396 A1 | 4/2003 | Michelson |
| 2003/0109928 A1 | 6/2003 | Pasquet |
| 2003/0125739 A1 | 7/2003 | Bagga et al. |
| 2003/0130739 A1 | 7/2003 | Gerbec et al. |
| 2003/0135279 A1 | 7/2003 | Michelson |
| 2003/0220691 A1 | 11/2003 | Songer et al. |
| 2003/0236571 A1 | 12/2003 | Ralph et al. |
| 2004/0002761 A1 | 1/2004 | Rogers et al. |
| 2004/0006393 A1 | 1/2004 | Burkinshaw |
| 2004/0010318 A1 | 1/2004 | Ferree |
| 2004/0019354 A1 | 1/2004 | Johnson et al. |
| 2004/0054413 A1 | 3/2004 | Higham et al. |
| 2004/0059421 A1 | 3/2004 | Glenn et al. |
| 2004/0064144 A1 | 4/2004 | Johnson et al. |
| 2004/0111155 A1 | 6/2004 | Ferree |
| 2004/0127994 A1 | 7/2004 | Kast et al. |
| 2004/0162618 A1 | 8/2004 | Mujwid et al. |
| 2004/0172134 A1 | 9/2004 | Berry |
| 2004/0186576 A1 | 9/2004 | Biscup et al. |
| 2004/0220580 A1 | 11/2004 | Johnson et al. |
| 2004/0220672 A1 | 11/2004 | Shadduck |
| 2004/0225363 A1 | 11/2004 | Richelsoph |
| 2004/0230198 A1 | 11/2004 | Manzi et al. |
| 2004/0267366 A1 | 12/2004 | Kruger |
| 2004/0267367 A1 | 12/2004 | O'Neil |
| 2005/0010290 A1 | 1/2005 | Hawkins |
| 2005/0010295 A1 | 1/2005 | Michelson |
| 2005/0015150 A1 | 1/2005 | Lee |
| 2005/0033424 A1 | 2/2005 | Fell |
| 2005/0055097 A1 | 3/2005 | Grunberg et al. |
| 2005/0131543 A1 | 6/2005 | Benzel et al. |
| 2005/0154463 A1 | 7/2005 | Trieu |
| 2005/0154465 A1 | 7/2005 | Hodges et al. |
| 2005/0187633 A1 | 8/2005 | Ferree |
| 2005/0203599 A1 | 9/2005 | Garabedian et al. |
| 2005/0234555 A1 | 10/2005 | Sutton et al. |
| 2005/0240267 A1 | 10/2005 | Randall et al. |
| 2005/0273178 A1 | 12/2005 | Boyan et al. |
| 2006/0004454 A1 | 1/2006 | Ferree et al. |
| 2006/0025861 A1 | 2/2006 | McKay |
| 2006/0058807 A1 | 3/2006 | Landry et al. |
| 2006/0058880 A1 | 3/2006 | Wysocki et al. |
| 2006/0069438 A1 | 3/2006 | Zucherman et al. |
| 2006/0106462 A1 | 5/2006 | Tsou |
| 2006/0142858 A1 | 6/2006 | Colleran et al. |
| 2006/0142862 A1 | 6/2006 | Diaz et al. |
| 2006/0149383 A1 | 7/2006 | Arnin et al. |
| 2006/0167550 A1 | 7/2006 | Snell et al. |
| 2006/0173542 A1 | 8/2006 | Shikinami |
| 2006/0178745 A1 | 8/2006 | Bartish et al. |
| 2006/0189999 A1 | 8/2006 | Zwirkoski |
| 2006/0190083 A1 | 8/2006 | Arnin et al. |
| 2006/0195191 A1 | 8/2006 | Sweeney et al. |
| 2006/0212118 A1 | 9/2006 | Abernathie |
| 2006/0235535 A1 | 10/2006 | Ferree et al. |
| 2006/0247778 A1 * | 11/2006 | Ferree et al. ............... 623/17.14 |
| 2006/0247781 A1 | 11/2006 | Francis |
| 2006/0259144 A1 | 11/2006 | Trieu |
| 2006/0264965 A1 | 11/2006 | Shadduck et al. |
| 2006/0293756 A1 * | 12/2006 | Felt ........................... 623/17.16 |
| 2007/0027546 A1 | 2/2007 | Palm |
| 2007/0032874 A1 | 2/2007 | Lee et al. |
| 2007/0050036 A1 | 3/2007 | Felt |
| 2007/0233255 A1 | 10/2007 | Song et al. |
| 2007/0244485 A1 | 10/2007 | Greenhalgh et al. |
| 2008/0039942 A1 * | 2/2008 | Bergeron ................... 623/17.16 |
| 2008/0065220 A1 | 3/2008 | Alleyne et al. |
| 2008/0119853 A1 | 5/2008 | Felt et al. |
| 2008/0133017 A1 * | 6/2008 | Beyar et al. ............... 623/17.16 |
| 2008/0140206 A1 * | 6/2008 | Felt ........................... 623/17.16 |
| 2008/0208343 A1 | 8/2008 | Felt |
| 2008/0234820 A1 | 9/2008 | Felt et al. |
| 2008/0249622 A1 | 10/2008 | Gray |
| 2008/0262622 A1 | 10/2008 | Butler |
| 2009/0069895 A1 | 3/2009 | Gittings et al. |
| 2009/0138086 A1 * | 5/2009 | Dewey ....................... 623/17.16 |
| 2009/0276047 A1 | 11/2009 | Felt et al. |
| 2010/0030338 A1 | 2/2010 | Simon |
| 2010/0057144 A1 | 3/2010 | Felt et al. |
| 2010/0145457 A1 | 6/2010 | Felt et al. |
| 2011/0270399 A1 | 11/2011 | Yurek et al. |

FOREIGN PATENT DOCUMENTS

| | | |
|---|---|---|
| DE | 198 23 325 | 3/2000 |
| EP | 0 353 936 | 2/1990 |
| EP | 0 378 002 | 7/1990 |
| EP | 0 505 634 | 9/1992 |
| EP | 0 521 573 | 1/1993 |
| EP | 1752116 A1 | 2/2007 |
| FR | 2 639 823 | 6/1990 |
| FR | 2781998 | 2/2000 |
| WO | WO 98/20939 | 5/1988 |
| WO | WO 93/11723 | 6/1993 |
| WO | WO 95/30388 | 11/1995 |
| WO | WO 95/31946 | 11/1995 |
| WO | WO 95/31948 | 11/1995 |
| WO | WO 97/26847 | 7/1997 |
| WO | WO 99/44509 | 9/1999 |
| WO | WO99/56800 | 11/1999 |
| WO | WO 99/61084 | 12/1999 |
| WO | WO00/13619 | 3/2000 |
| WO | WO 00/59411 | 10/2000 |
| WO | WO 01/66021 | 9/2001 |
| WO | WO02/17821 | 3/2002 |
| WO | WO03/099171 | 12/2003 |
| WO | WO 2004/098466 | 11/2004 |
| WO | WO2005051246 | 6/2005 |
| WO | WO2006051547 | 5/2006 |

(56) References Cited

FOREIGN PATENT DOCUMENTS

| WO | WO 2006/127848 A2 | 11/2006 |
|---|---|---|
| WO | WO 2006/127849 A2 | 11/2006 |

OTHER PUBLICATIONS

Chinese Office Action Patent Application No. 201380013982.1 dated Aug. 26, 2015. English transalation provided.
IPRP and Written Opinion for International Application No. PCT/US2013/032786 dated Sep. 25, 2014.
European Office Action for European Application No. 06771111.9 dated Jul. 19, 2013.
Japanese Office Action for Japanese Application No. 2009-538404 dated Jul. 30, 2013. English Translation Provided.
International Search Report and Written Opinion for International Application No. PCT/US2013/032786 dated Aug. 19, 2013.
Chinese 3rd Office Action for Chinese Application No. 200680018453.0 dated Dec. 13, 2012.
Chinese Office Action for Chinese Application No. 200780050196.3 dated Jan. 14, 2013.English Translation not available.
JP Notice of Reasons for Rejection for JP Application No. 2009-538404 dated Sep. 18, 2012.
Chinese Office Action for Chinese Application No. 200780050196.3 dated Apr. 27, 2012.English Translation not available.
European Search Report for European Application No. EP07853144 dated Mar. 23, 2012.
Notification of International Preliminary Report on Patentability for International Application No. PCT/US06/20152 dated Jun. 29, 2012.
European Search Report for European Application No. EP06771111 dated Mar. 21, 2012.
International Search Report for International Application No. PCT/US2006/000558 dated Jul. 18, 2006.
International Preliminary Report on Patentabilty for International Application No. PCT/US2007/024262 dated Jun. 4, 2009.
International Search Report for International Application No. PCT/US06/20152 dated Sep. 12, 2008.
International Search Report for International Application No. PCT/US07/24262 dated Oct. 30, 2008.
Spine-Tech, Inc., "Summary of Safety and Effectiveness," May 23, 2996, 100 pages, Minneapolis, Minnesota.
RSB Spine, LLC, "510(k) Summary," Sep. 18, 2007, 4 pages, Cleveland, Ohio.
Synthes Spine, "510 (k) Summary—Revised Sep. 2007" 5 pages, Sep. 14, 2007West Chester, Pennsylvania.
Shin et al., "Posterior Lumbar Interbody Fusion via a Unilateral Approach," Yonsei Medical Journal, 2006, vol. 47, pp. 319-325.
Toth et al., "Polyehteretherketone as a biomaterial for spinal applications," Biomaterials, 2006, pp. 324-334.
Vadapalli et al., "Biomechanical Rationale for Using Polyetheretherketone (PEEK) Spacers for Lumbar Interbody Fusion—A Finite Element Study," SPINE, 2006, vol. 31, No. 26, pp. E992-E998.
Powers et al., "Minimally Invasive Fusion and Fixation Techniques," Neurosurg. Clin N Am, 2006, pp. 477-489.
Vertebral Technologies, "InterFuse ® Interbody Fusion System," 2009, pamphlet.
An et al., "The Future of Spinal Fuzion. Txt." ORTHO SuperSite, Aug. 2006 pp. 1-3.
Andersson et al., "Macintosh Arthroplasty in Rheumatoid Arthritis," Department of Orthopaedic Surgery and Department of Rheumatology, The London Hospital, London, England, 1974, pp. 245-259.
Cameron et al., "Review ofa Failed Knee Replacement and Some Observations on the Design of a Knee Resurfacing Prosthesis," Archives of Orthopaedic and Traumatic Surgery, vol. 97, No. 1, 1980, pp. 87-89.
Clary et al., "Experience with the MacIntosh Knee Prosthesis," Southern Medical Journal, Journal of the Southern Medical Association, Mar. 1972, vol. 65, No. 3, pp. 265-272.
Conaty, "Surgery of the Hip and Knee in Patients with Rheumatoid Arthritis," The Arthritis Servie (surgery) of Rancho, Los Amigos Hospital, Downey, Mar. 1973, vol. 55-A, No. 2, pp. 301-314.
Emerson et al., "The Use of the McKeever metallic Hemiarthroplasty for Unicompartmental Arthritis," The Journal of Bone and Joint Surgery, 1985, pp. 208-212.
Hastings, "Double Hemiarthroplasty of the Knee in Rheumatoid Arthritis," The Journal of Bone and Joint Surgery, Feb. 1973, vol. 55 B, No. 1, pp. 112-118.
Jessop et al., "Follow-up of the Macintosh Arthroplasty of the Knee Joint," Rheum. Phys. Med., 1972, vol. XI, No. 5, pp. 224.
Kay et al., "The Macintosh Tibial Plateau Hemiprosthesis for the Rheumatoid Knee," The Journal of Bone and Joint Surgery, May 1972, vol. 54B, No. 2, pp. 256-262.
Kozinn et al., "Surgical Treatment of Unicompartmental Degenerative Arthritis of the Knee," Rheumatic Disease Clinics of North America, Dec. 1988, vol. 14, No. 3, pp. 545-564.
MacIntosh et al., "The Use of the Hemiarthroplasty Prosthesis for Advanced Osteoarthritis and Rheumatoid Arthritis of the Knee," The Journal of Bone and Joint Surgery,May 1972, vol. 54 B, No. 2, pp. 244-255.
McCallum et al., "Duplication of Medial Erosion in Unicompartmental Knee Arthroplasties," The Journal of Bone and Joint Surgery, 1995, pp. 726-728.
McCollum et al., "Tibial Plateau Prosthesis in Arthroplasty of the Knee," The Journal of Bone and Joint Surgery, Jun. 1970, vol. 52-A., No. 4, pp. 827-828.
McKeever, "Tibial Plateau Prosthesis," The Classic, pp. 3-12. Jan.-Feb. 1985.
Porter, "MacIntosh Athroplasty: a long-term review," J.R. Coll. Surg. Edinb., Aug. 1988, vol. 33, pp. 199-201.
Potter, "Arthroplasty of the Knee in Rheumatoid Arthritis and Osteoarthritis," The Journal of Bone and Joint Surgery, Jan. 1972, vol. 54A, No. 1, pp. 1-24.
Potter, "Arthroplasty of the Knee with Tibial Metallic Implants of the McKeever and MacIntosh Design," Surgical Clinics of North America, Aug. 1969, vol. 49, No. 4, pp. 903-915.
Sbarbaro, "Hemitibial plateau prosthesis ten years experience in 500 knee arthroplasties," Acta Orthopaedica Belgica, 1973, pp. 91-100.
Schorn et al., "MacIntosh Arthroplasty in Rheumatoid Arthritis," Rheumatology and Rehabilitation, vol. XVII, No. 3, pp. 155-163. 1978.
Scott et al., "McKeever Metallic Hemiarthroplasty of the Knee in Unicompartmental Degenerative Arthritis," The Journal of Bone and Joint Surgery, Feb. 1985, vol. 67-A, No. 2, pp. 203-207.
Stauffer et al., "The MacIntosh Prosthesis, Prospective Clinical and Gait Evaluation," Arch Surg, Jun. 1975, vol. 110, pp. 717-720.
Swanson et al., "Unicompartmental and Bicompartmental Arthroplasty of the Knee with a Finned Metal Tibial-Plateau Implant," The Journal of Bone and Joint Surgery, Oct. 1985, vol. 67-A, No. 8, pp. 1175-1182.
Taylor et al., "MacIntosh arthroplasty in rheumatoid arthritis," Proceedings and Reports of Universities, Colleges, Councils and Associations, pp. 119-120.
Wayne, "Use of the McIntosh Prosthesis in Surgical Reconstruction of the Knee," Abstracts of the 1971 Proceedings, Jun. 1972, No. 85, pp. 292-293.
Wordsworth et al., "MacIntosh Arthroplasty for the rheumatoid knee: a 10-year follow up," Annals of the Rheumatic Diseases, 1985, pp. 738-741.
Chinese Office Action for Chinese Application No. 200680018453.0 dated Jan. 12, 2011.
Japanese Office Action for Japanese Application No. 2008-513686 dated Feb. 1, 2011. (translation).
Chinese Office Action for Chinese Application No. 200680034261.9 dated Jun. 4, 2010.
Tan et al., Interbody Device Shape and Size are Important to Strengthen the Vertebra—Implant Interface, Spine 2005. vol. 30, No. 6. pp. 638-644.
Ryortho, "Here comes ProDisc" Orthopedics This Week, vol. 2, Issue 3. (published prior to Jan. 19, 2006).

(56) References Cited

OTHER PUBLICATIONS

Australian Office Action for Australian patent application No. 2010200382 dated Mar. 24, 2011.
Get ADR.com Top Surgeons—Latest Orthopedic Options. Nov. 29, 2005. 2 pages http://www.getadr.com/link.htm.
Zwillich, Artifical Spinal Disc Nears Approval. WebMD Medical News. Nov. 29, 2005. 4 pages. http://www.webmd.com/content/article/88/9801.htm.
Get ADR.com Top Surgeons—Latest Orthopedic Options. Nov. 29, 2005. 2 pages. http://www.getadr.com/maverick.htm.
Cluett, "Discetomy-Spinal Surgery to remove herniated disc", Nov. 29, 2005. 3 pages. http://orthopedica.about.com/cs/herniateddisk/a/repturedisk_3.htm.
Get ADR.com Top Surgeons—Latest Orthopedic Options (Artificial Disc Replacement) . Nov. 29, 2005. 3 pages http://www.getadr.com.
Get ADR.com Top Surgeons—Latest Orthopedic Options (Prestige Cervical ADR) . Nov. 29, 2005. 3 pages http://www.getadr.com/prestige.htm.
Details of Second Office Action for Chinese Application No. 200680018453.0 dated Mar. 26, 2012.

\* cited by examiner

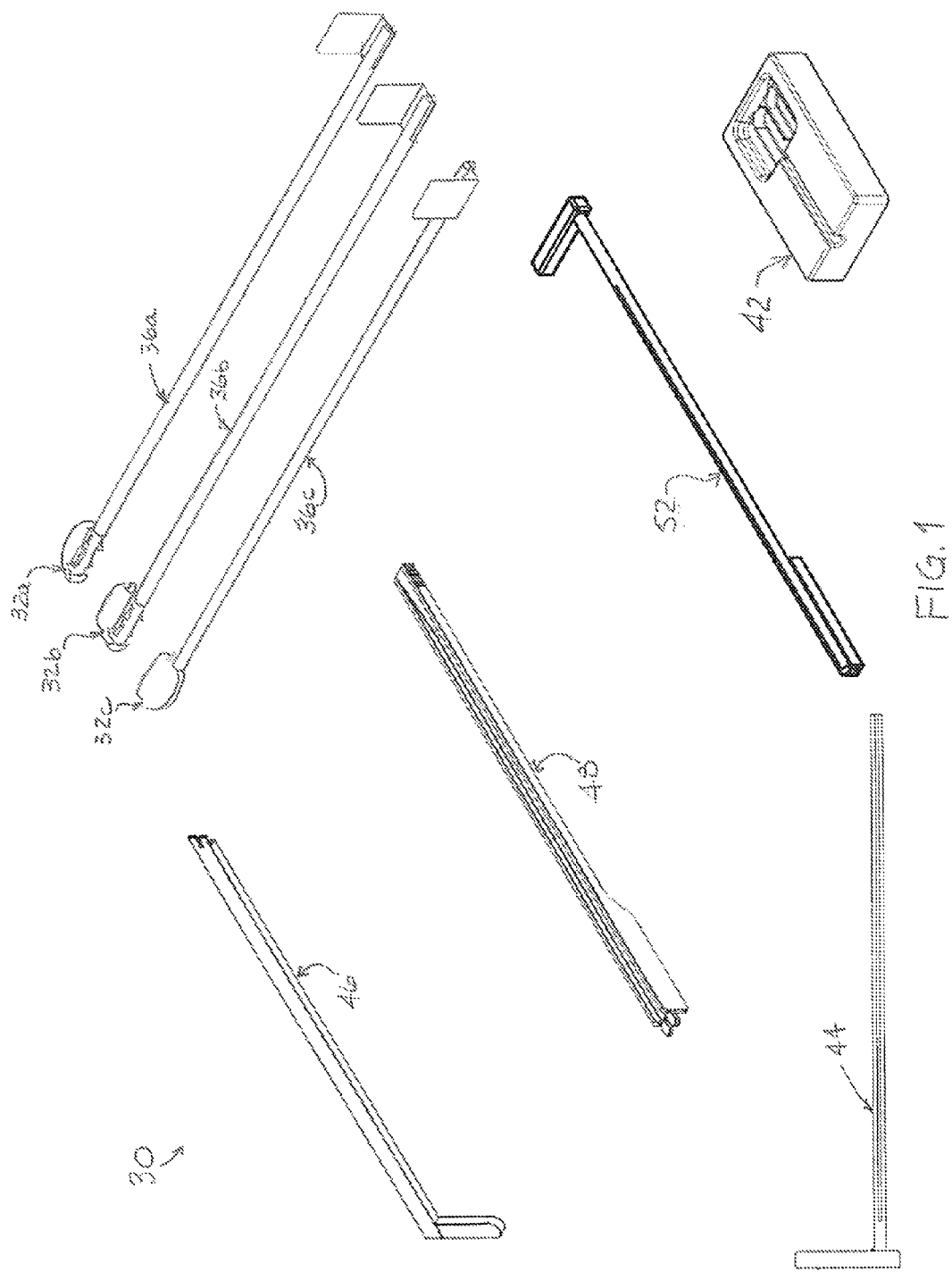

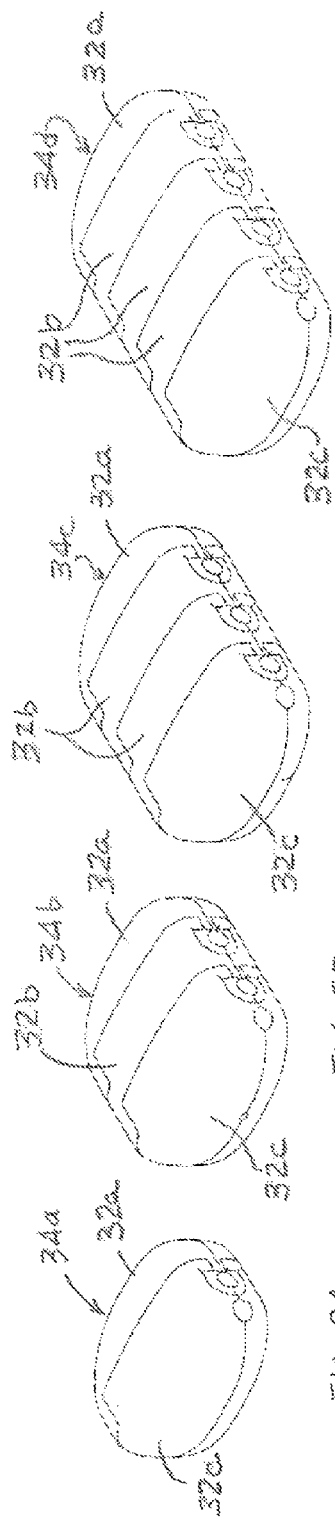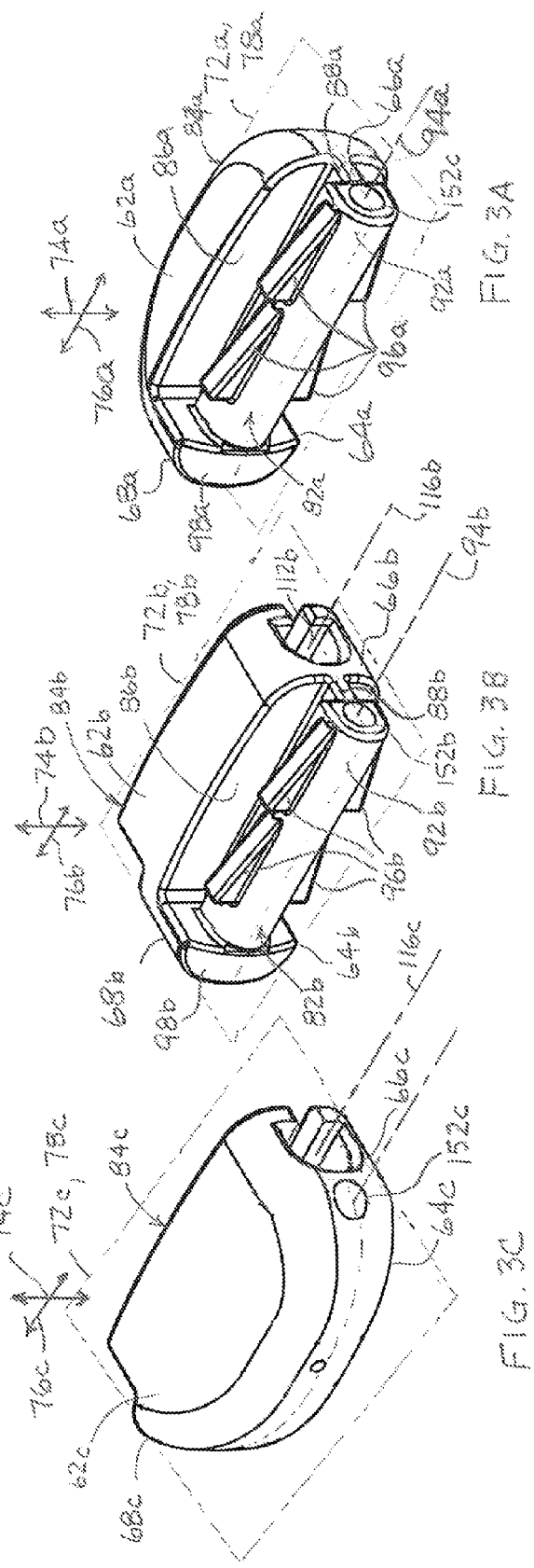

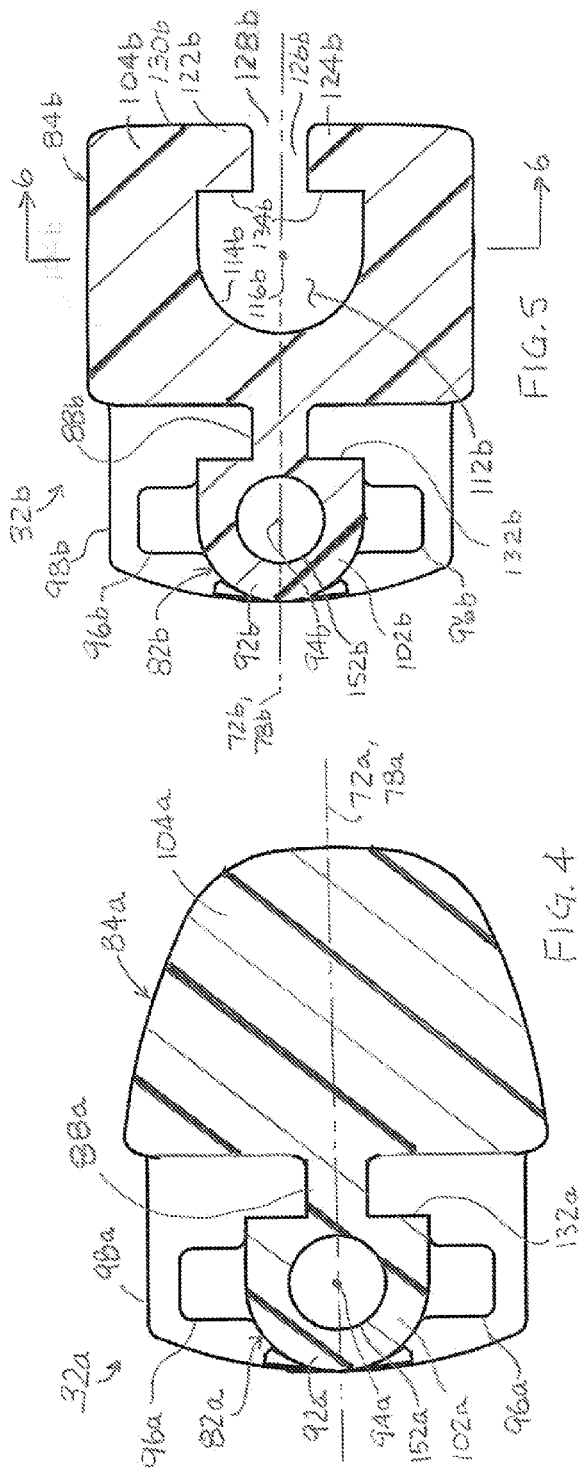
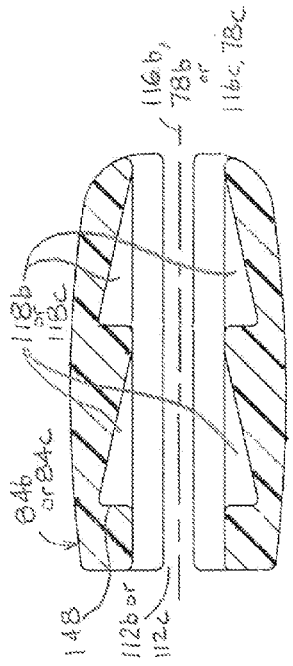
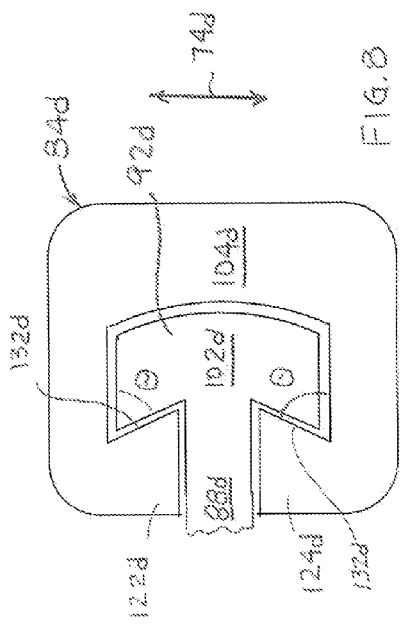

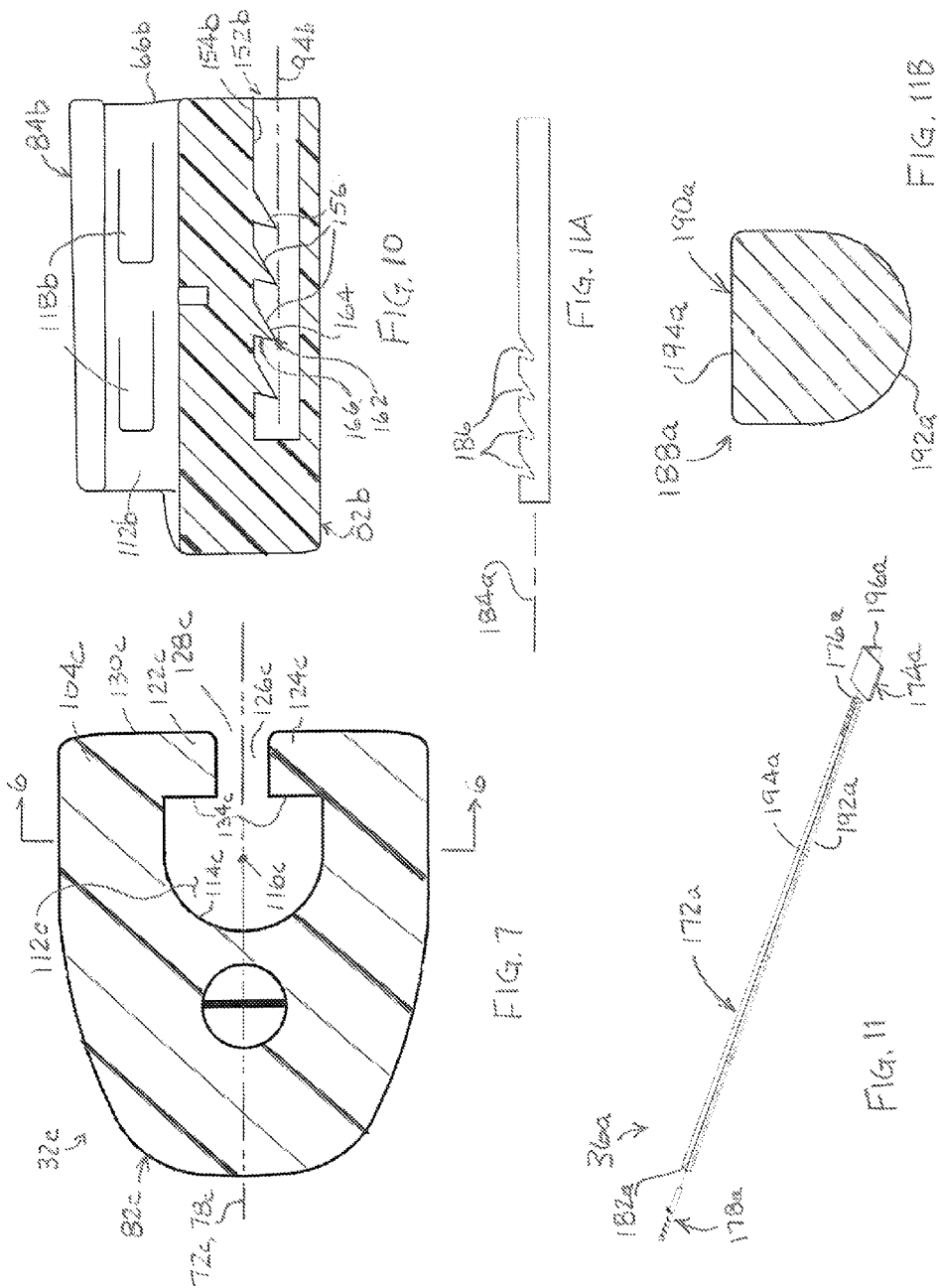

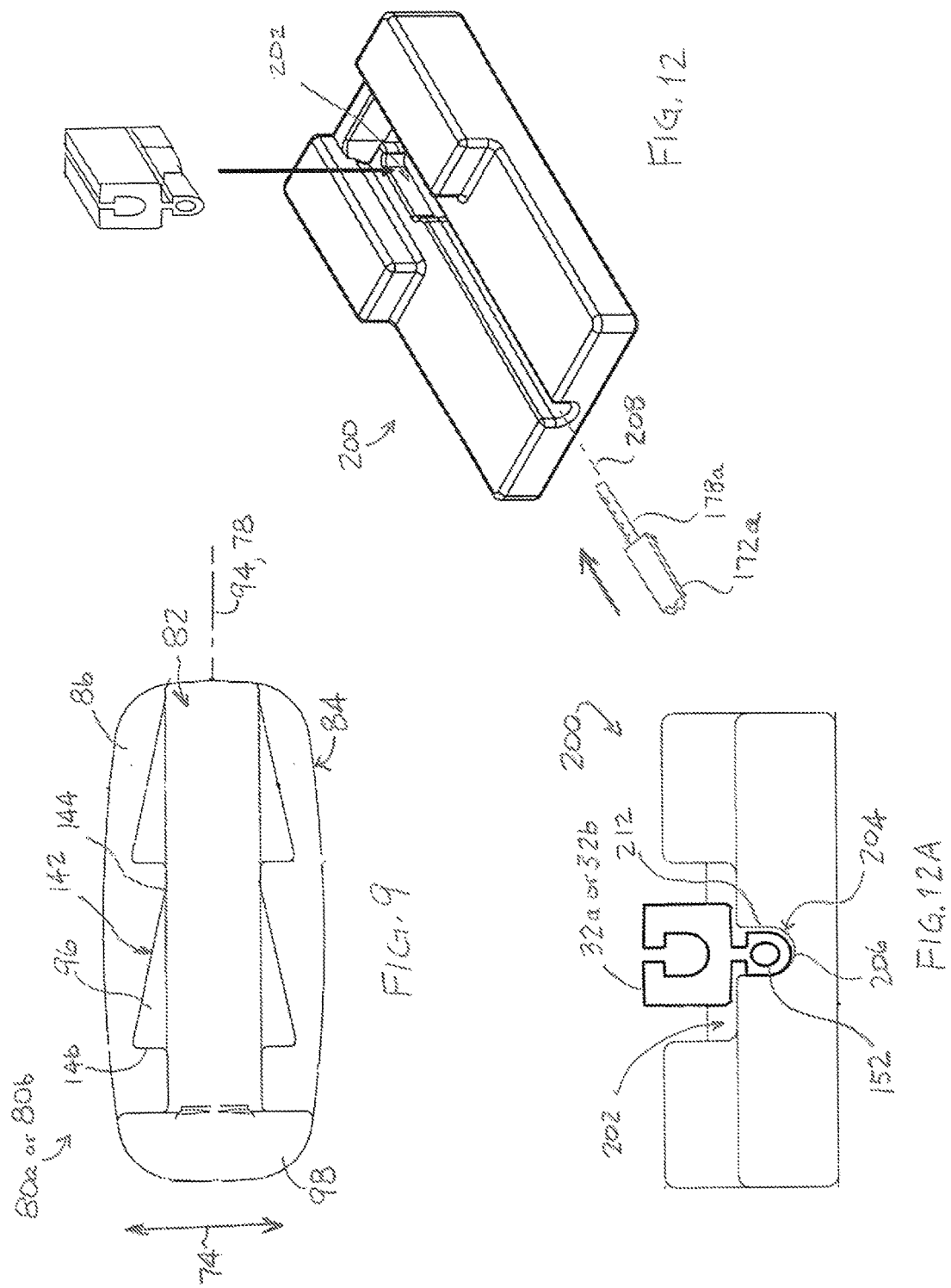

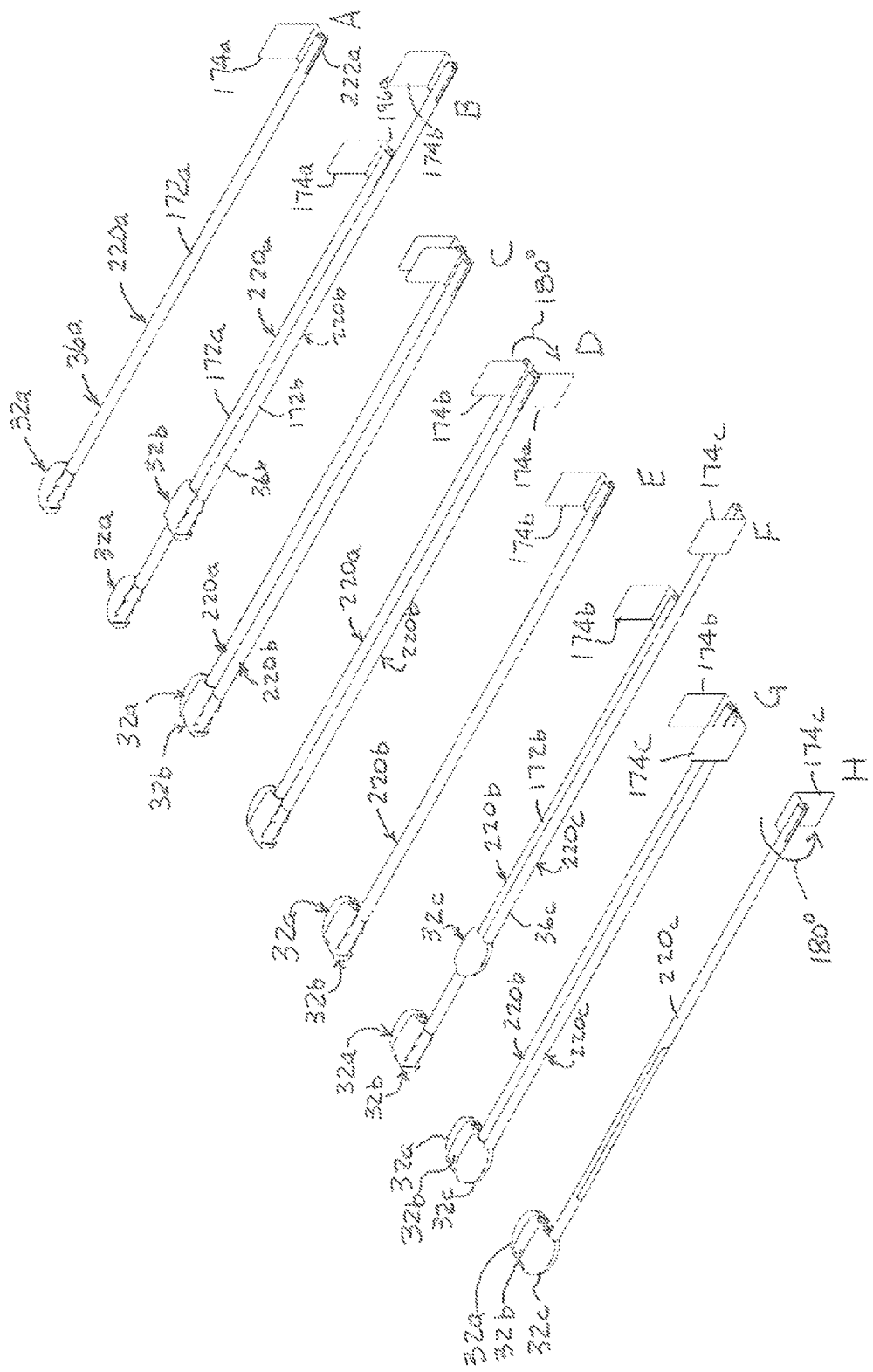

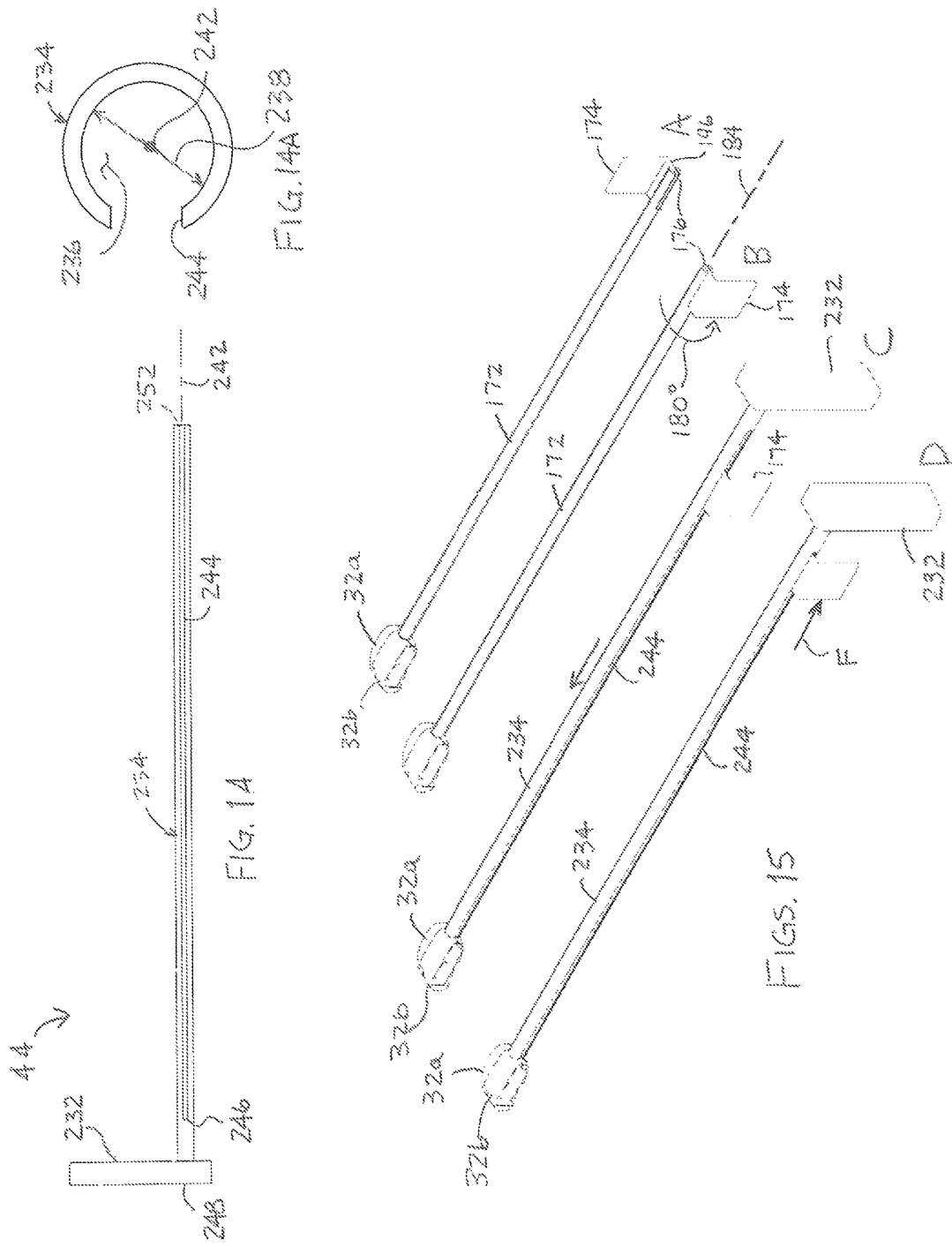

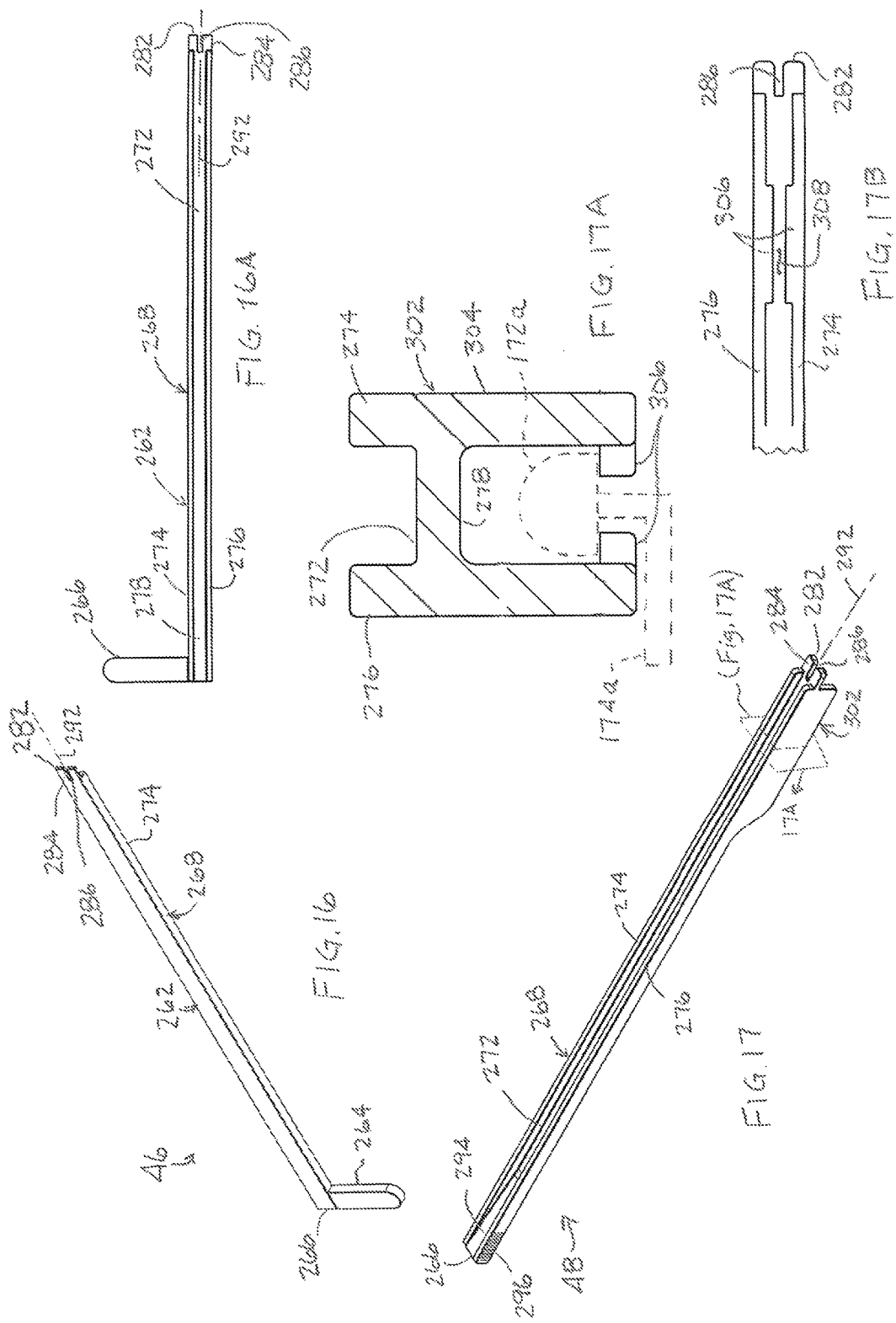

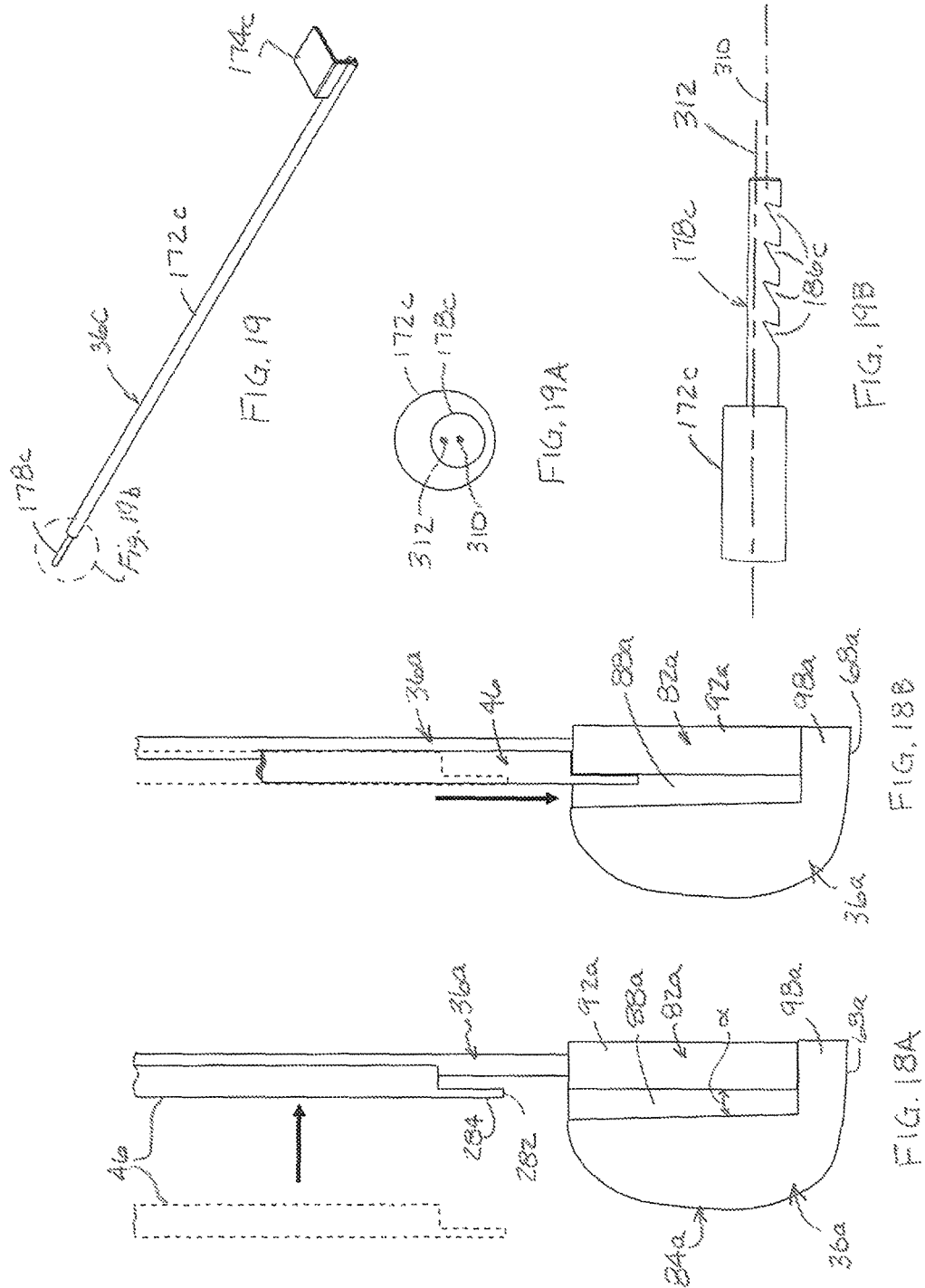

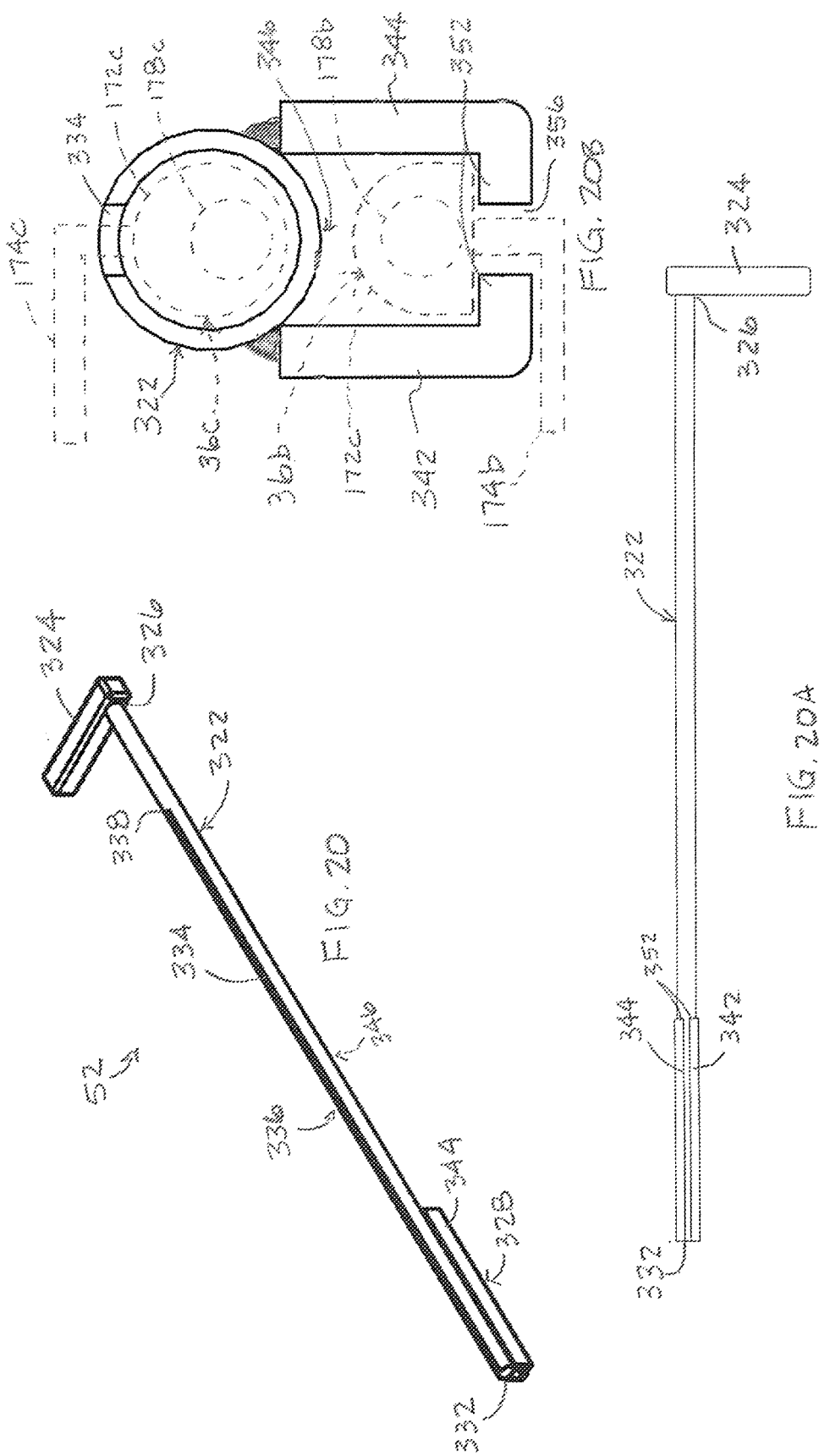

MODULAR SEGMENTED DISC NUCLEUS IMPLANT

RELATED APPLICATIONS

This application claims the benefit of U.S. Provisional Application No. 61/685,383, filed Mar. 16, 2012, the disclosure of which is incorporated herein in its entirety except for express definitions contained therein.

BACKGROUND

The use of segmented spinal implants where the segments are implanted sequentially using insertion guides for so-called "minimally invasive" surgical techniques is known. United States Patent Application No. 2008/0133017 to Beyar, et al. (hereinafter "Beyar") discloses a two-level, motion preserving total disc replacement system using dual-level segments, each segment comprising a top "slice" and a bottom "slice" in order to construct both levels of the motion-preserving device.

U.S. Pat. No. 7,591,853 to Felt, et al. (hereinafter "Felt") discloses a segmented disc nucleus implant that includes a hard inner core surrounded by a compliant outer shell. While the compliant outer shell facilitates motion preserving aspects, the inner core can be constructed of harder materials such as polyetheretherketone (PEEK) to facilitate structures for reliably interlocking the segments.

A system that, like the device of Felt but unlike the device of Beyar, replaces only the disc nucleus for enhanced reduced invasiveness, and that further enhances the motion preserving aspects of the device of Felt would be welcomed.

SUMMARY

Various embodiments of the invention include a segmented nucleus disc prosthesis made of a single compliant material homogeneously throughout the prosthesis. The compliant material provides a disc nucleus implant that more closely mimics the motion of a natural disc nucleus than the other segmented motion-preserving devices available. The segmented aspect enables implantation of the device with reduced invasiveness, as well as a modular design that enables prostheses of varying dimension to be constructed from modular segment "building blocks."

Heretofore, the presence of harder materials was thought necessary to facilitate the interlocking. Thus, the segmented implants of Beyar and Felt have included interlocking structures comprising hard materials such as metals and PEEK. The presence of these hard materials can affect the complexity of the design of motion preserving devices, or limit the motion of the spine relative to a natural disc nucleus. The disclosed invention differs from Beyar and Felt in that the interlocking modular segments do not include hard materials to facilitate the interlocking aspects. Rather, the interlocking modular segments of various embodiments of the invention are made of a single compliant material. Furthermore, Beyar teaches a total disc replacement, rather than a disc nucleus replacement, and is therefore generally more invasive than the present invention.

Structurally, various aspects of the embodiments of the invention are directed to enable affirmative interlocking of the segments despite the use of the compliant material. In certain embodiments, a plurality of modular segments is included, each including a superior side, an inferior side, a proximal end, and a distal end opposite the proximal end. The superior and inferior sides are disposed on opposing faces of a transverse plane of the respective modular segment, the transverse plane being orthogonal to a superior/inferior coordinate of the respective modular segment when in an implanted configuration. In some embodiments, transverse plane corresponds to a central transverse plane. Each of the plurality of modular segments are adapted to interlock with an adjacent one of the plurality of modular segments in a side-by-side arrangement on the transverse plane when in the implanted configuration. The plurality of modular segments can comprise a first end modular segment including a first end body portion and a first end rail portion, the first end rail portion extending from a flanking face of the first end body portion the first end rail portion defining a first end rail axis that passes through the proximal end and the distal end of the first end modular segment. The first end rail axis lies on the transverse plane of the first end modular segment. The first end rail portion includes a plurality of diametrically opposed barbs that extend radially outward relative to the first end rail axis and parallel to the superior/inferior coordinate of the first end modular segment, the first end rail portion having a first end rail cross-section that is normal to the first end rail axis. In one embodiment, the first end rail portion includes a web and a rail head, the web being disposed between the rail head and the flanking face and extending along the transverse plane. The rail head can include planar faces that intersect the web at one of a right angle and an acute angle.

The prosthesis can further comprise an opposing end modular segment including a body portion that defines an opposing end elongate slot having an interior surface, the opposing end elongate slot passing through the body portion of the opposing end modular segment to define an opposing end slot axis, the opposing end slot axis lying on a transverse plane that is normal to the superior/inferior coordinate of the opposing end modular segment. The body portion of the opposing end modular segment defines an opposing end body cross-section normal to the opposing end slot axis, the body portion of the opposing end modular segment further defining a plurality of recesses that are recessed from the interior surface of the opposing end elongate slot. Each of the plurality of recesses can extend radially outward relative to the opposing end slot axis and parallel to the superior/inferior coordinate of the opposing end modular segment.

The body portion of the opposing end modular segment can include a superior lip portion and an inferior lip portion, each of the lip portions being adjacent the opposing end elongate slot and extending parallel to the opposing end slot axis and each protruding toward the transverse plane of the opposing end modular segment. Each of the superior lip portion and the inferior lip portion of the opposing end modular segment can define an interior face that complements the planar faces of the rail head. In one embodiment, the first end rail portion defines a first mounting port accessible from the proximal end of the first end modular segment. The first end segment can further comprise a stop portion at the distal end of the first segment.

In one embodiment, the opposing end body cross-section can be complementary to the first end rail cross-section of the first end rail portion for sliding engagement between the first end modular segment and the opposing end modular segment along the first end rail axis. Each of the plurality of recesses of the opposing end modular segment can be positioned and dimensioned complementary to a corresponding one of the plurality of barbs of the first end modular segment. The diametrically opposed barbs of the first end rail portion are adapted for capture within the plurality of recesses of the body portion of the opposing end modular segment when in the implanted configuration. The first end modular segment and the opposing end modular segment can be adapted to interlock with each other to define an implanted configuration presenting a generally continuous periphery that generally corresponds to the evacuated nucleus disc space.

In another embodiment the plurality of modular segments that make up the prosthesis includes an intermediate modular segment having an intermediate body portion and an intermediate rail portion. The intermediate rail portion extends from a flanking face of the intermediate body portion, the intermediate rail portion defining an intermediate rail axis that passes through the proximal end and the distal end of the intermediate modular segment. The intermediate rail portion can include a plurality of diametrically opposed barbs that extend radially outward relative to the intermediate rail axis and parallel to the superior/inferior coordinate of the intermediate modular segment. The intermediate rail portion defines an intermediate cross-section normal to the intermediate rail axis.

The intermediate body portion defines an intermediate elongate slot having an interior surface, the intermediate elongate slot passing through the intermediate body portion to define an intermediate slot axis. The intermediate rail axis and the intermediate slot axis can be substantially parallel to each other and lying on the transverse plane of the intermediate modular segment, the intermediate body portion defining an intermediate body cross-section normal to the intermediate slot axis. The body portion of the intermediate modular segment can further defining a plurality of recesses that are recessed from the interior surface of the intermediate elongate slot and extend radially outward relative to the intermediate slot axis and parallel to the superior/inferior coordinate of the intermediate modular segment. In one embodiment, the intermediate body portion includes a superior lip portion and an inferior lip portion, each being adjacent the intermediate elongate slot and extending parallel to the intermediate slot axis and each protruding toward the transverse plane of the intermediate modular segment.

In one embodiment of the invention, the intermediate body cross-section is complementary to the first end rail cross-section of the first end rail portion for sliding engagement between the first end modular segment and the intermediate modular segment along the first end rail axis. Each of the plurality of recesses of the intermediate modular segment can be positioned and dimensioned complementary to a corresponding one of the plurality of diametrically opposed barbs of the first end modular segment. The diametrically opposed barbs of the first end rail portion can be configured for capture within the plurality of recesses of the intermediate modular segment when in the implanted configuration. In this embodiment, the opposing end body cross-section is complementary to the intermediate rail cross-section for sliding engagement between the opposing end modular segment and the intermediate modular segment along the intermediate rail axis. Each of the plurality of recesses of the opposing end modular segment can be positioned and dimensioned complementary to a corresponding one of the plurality of diametrically opposed barbs of the intermediate modular segment. The diametrically opposed barbs of the intermediate rail portion can be adapted for capture within the plurality of recesses of the body portion of the opposing end modular segment when in the implanted configuration. The first end modular segment can be adapted to interlock with the intermediate modular segment and the intermediate modular segment being adapted to interlock with the opposing end modular segment to define an implanted configuration presenting a generally continuous periphery that generally corresponds to the evacuated nucleus disc space.

In various embodiments, each modular segment is of a homogenous material having a compressive modulus between about 2 and about 100 MPa.

In various embodiments, each of the plurality of modular segments includes structure defining a mounting port disposed on and accessible from the proximal end, the mounting port including an interior surface and a plurality of detents that extend from a first side of the interior surface, wherein a second side opposite the first side defines a cylindrical surface.

In another embodiment of the invention, a system for configuring the modular disc nucleus prosthesis includes a plurality of insertion tools, one for each of the plurality of segments and each including a tip portion having a plurality of notches formed on one side thereof, the tip portion extending along a rotation axis and being dimensioned for insertion into the mounting ports of the modular segments, the notches being configured to mate with the detents within the mounting port. The tip portion can be selectively releasable from the corresponding one of the mounting ports by rotating the insertion tool about the central axis.

Various embodiments of the invention are suitable for implantation from any direction relative to the superior/inferior coordinate (i.e., a posterior, anterior or lateral approach, or any approach in between).

BRIEF DESCRIPTION OF THE DRAWINGS

FIG. 1 depicts various components of a disc nucleus replacement system in an embodiment of the invention;

FIGS. 2A through 2D are perspective views of various modular disc nucleus prostheses embodiments of the invention;

FIGS. 3A through 3C are perspective views of individual modular segments of the prostheses of FIGS. 2A through 2D in embodiments of the invention;

FIG. 4 is a sectional view of a first end modular segment ("A-segment") in an embodiment of the invention;

FIG. 5 is a sectional view of an intermediate modular segment ("B-segment") in an embodiment of the invention;

FIG. 6 is a sectional view of an elongate slot portion of the modular segments of FIGS. 4 and 5 in an embodiment of the invention;

FIG. 7 is a sectional view of an opposing end modular segment ("C-segment") in an embodiment of the invention;

FIG. 8 is a partial sectional view of an alternative rail portion and body portion configuration in an embodiment of the invention;

FIG. 9 is a side view of an A-segment or a B-segment in an embodiment of the invention;

FIG. 10 is a sectional view of a B-segment at the transverse plane in an embodiment of the invention;

FIG. 11 is an exploded view of an A/B insertion tool in an embodiment of the invention;

FIG. 11A is an enlarged, elevation view of a tip portion of the A/B insertion tool of FIG. 11 in an embodiment of the invention;

FIG. 11B is a sectional view of the "D-shaped" shaft portion of the A/B insertion tool of FIG. 11 in an embodiment of the invention;

FIG. 12 is a perspective view of an assembly of an A- or B-segment/insertion tool assembly in an embodiment of the invention;

FIG. 12A is an elevational view of the assembly of FIG. 12;

FIGS. 13A through 13H depict the assembly of a modular nuclear disc prosthesis in an embodiment of the invention;

FIG. 14 is a side view of a removal tool in an embodiment of the invention;

FIG. 14A is a sectional view of the removal tool of FIG. 14;

FIGS. 15A through 15D depict operation of the removal tool of FIG. 14 in an embodiment of the invention;

FIG. 16 is a perspective view of an A-segment stabilizer in an embodiment of the invention;

FIG. 16A is a side view of the A-segment stabilizer of FIG. 16 in an embodiment of the invention;

FIG. 17 is a perspective view of a B-segment stabilizer in an embodiment of the invention;

FIG. 17A is a sectional view of the B-segment stabilizer of FIG. 17 in an embodiment of the invention;

FIG. 17B is a partial plan view of the B-segment stabilizer of FIG. 17 in an embodiment of the invention;

FIGS. 18A and 18B are plan views depicting the coupling of the A-segment stabilizer to an A-segment/insertion tool assembly in an embodiment of the invention;

FIG. 19 is a perspective view of a C-segment insertion tool in an embodiment of the invention;

FIG. 19A is an end view of the C-segment insertion tool in an embodiment of the invention;

FIG. 19B is a partial elevational view of the tip portion of the C-segment insertion tool of FIG. 19 in an embodiment of the invention;

FIG. 20 is a perspective view of a C-segment stabilizer C-segment insertion tool in an embodiment of the invention;

FIG. 20A is an elevational view of the C-segment stabilizer C-segment insertion tool of FIG. 20 in an embodiment of the invention; and FIG. 20b is an end view of the C-segment stabilizer C-segment insertion tool of FIG. 20 in an embodiment of the invention.

DETAILED DESCRIPTION

Referring to FIG. 1, a disc nucleus replacement system 30 is depicted in an embodiment of the invention. The disc nucleus replacement system 30 includes modular segments 32a, 32b and 32c for assembly of modular disc nucleus prostheses 34a through 34d (FIG. 2) (hereinafter "the prosthesis" or "prostheses")", insertion tools 36a and 36c for installing the modular segments 32 of the prosthesis, and various tools to assist in the installation of the prosthesis, including a loading platform 42, a removal tool 44, an A-segment stabilizer 46, a B-segment stabilizer 48 and a C-segment stabilizer 52.

Throughout this disclosure, it is noted that certain components have numerical references consisting of a number followed by a letter suffix (e.g., modular segments 32a, 32b and 32c and insertion tools 36a and 36c above). Where this numbering convention is utilized, the number refers to the item generically or collectively, and the letter to the item in particular. Following this convention, when the number is referred to alone, the reference is to the item generically or collectively (e.g., modular segment(s) 32 or insertion rod(s) 36).

Referring to FIGS. 2A through 2D (referred to collectively as FIG. 2) and FIGS. 3A through 3C (referred to collectively as FIG. 3), various prostheses and the modular segments from which they are constructed are depicted in embodiments of the invention. Each prosthesis 32a through 32d includes a plurality of modular segments 32 (i.e., at least two segments) interlocked with each other. Each modular segment 32 includes a superior side 62, an inferior side 64, a proximal end 66, and a distal end 68 opposite the proximal end 66. The superior and inferior sides 62 and 64 of each modular segment 32 are disposed on opposing faces of a transverse plane 72a, 72b and 72c of the respective modular segment 32, the transverse planes 72a, 72b and 72c being orthogonal to a superior/inferior coordinate 74a, 74b and 74c of the respective modular segment 32a, 32b and 32c when in an implanted configuration. Proximal/distal coordinates 76a, 76b and 76c are also defined as orthogonal to the superior inferior coordinates 74a, 74b and 74c and extending in a direction from the proximal ends 66 to the distal ends 68. Each of the plurality of modular segments 32 are adapted to interlock with an adjacent one of the plurality of modular segments in a side-by-side arrangement relative to the respective transverse planes 72 when in the implanted configuration.

The superior and inferior sides 62 and 64 are so named to correspond with their orientation along a respective superior/inferior coordinate 74 or superior/inferior direction when the prosthesis 34 is installed in an implanted configuration within the human body. In one embodiment, the modular segments 32 of the prosthesis 34 can be symmetric about the transverse plane 72; that is, for this embodiment, the superior side 62 of each modular segment 32 is a mirror image of the inferior side 64 about the transverse plane 72, thus establishing the transverse plane 72 as a central transverse plane 78.

The prostheses depicted in FIG. 2 include up to three modular segment types, depicted in FIG. 3: the first end modular segment 32a, alternatively referred to herein as an "A" segment (FIG. 3A); the intermediate modular segment 32b, alternatively referred to herein as a "B" segment (FIG. 3B); and the opposing end modular segment 32c, alternatively referred to herein as a "C" segment (FIG. 3C). In various embodiments of the invention, prostheses 34 can include one or more B-segments 32b, or can have no B-segments 32b (i.e., the A-segment 32a is coupled directly to the C-segment 32c, as depicted in FIG. 2A). While the length, width and thickness dimensions of individual B-segments 32b can vary, the general characteristics are the same, as described below. In some embodiments employing multiple B-segments 32b, the B-segments 32b are identical.

Referring to FIG. 4 and again to FIG. 3A, the first end modular segment 32a (A-segment) is depicted in an embodiment of the invention. The first end modular segment 32a includes a body portion 84a and a rail portion 82a, the rail portion 82a extending from a flanking face 86a of the body portion 84a. In one embodiment, the rail portion 82a includes a web 88a and a rail head 92a, the flanking face 86a and the rail head 92a being separated by the web 88a. The rail head 92a can define a rail axis 94a that passes through the proximal and distal ends 66a and 68a of the modular segment 32a. The rail portion 82a can also include a plurality of diametrically opposed barb portions 96a that extend radially outward relative to the rail axis 94a and parallel to the superior/inferior coordinate 74a of the first end modular segment 32a. In one embodiment, the first end modular segment 32a includes a stop portion 98a located at the distal end 68a. Cross-sections 102a and 104a of the rail portion 82a and the body portion 84a, respectively, of the first end modular segment 32a are depicted at FIG. 4, the cross-sections 102a, 104a being normal to the rail axis 94a.

Herein, the rail portion 82a, rail axis 94a, rail portion cross-section 102a, body portion 82a and body portion cross-section 104a of the first end modular segment 32a are alternatively referred to as the first end rail portion 82a, first end rail axis 94a, first end rail cross-section 102a, first end body portion 82a, and first end body portion cross-section 104a, respectively, to clarify association with the first end modular segment 32a.

Referring to FIGS. 5 and 6 and again to FIG. 3B, the intermediate modular segment 32b (B-segment) is depicted in an embodiment of the invention. The intermediate modular segment 32b includes a body portion 82b and a rail portion 82b, the rail portion 82b extending from a flanking face 86b of the body portion 82b. In one embodiment, the rail portion 82b includes a web 88b and a rail head 92b, the flanking face 86b and the rail head 92b being separated by the web 88b. The rail head 92b can define a rail axis 94b that passes through the proximal and distal ends 66b and 68b of the modular segment 32b. The rail portion 82b can also include a plurality of diametrically opposed barb portions 96b that extend radially outward relative to the rail axis 94b and parallel to the superior/inferior coordinate 74b of the intermediate modular segment 32b. In one embodiment, the intermediate modular segment 32b includes a stop portion 98b located at its distal end. Cross-sections 102b and 104b of the rail portion 82b and the body portion 84b, respectively, of the intermediate modular segment 32b are depicted at FIG. 5, the cross-sections 102b, 104b being normal to the rail axis 94b.

The body portion 84b of the intermediate modular segment 32b defines an elongate slot 112b that passes through the body portion 84b and includes an interior surface 114b. The elongate slot 112b further defines a slot axis 116b that is substantially parallel to the intermediate rail axis 94b of the intermediate modular segment 32b. In one embodiment, the rail axis 94b and the slot axis 116b lie on the transverse plane 72b of the intermediate modular segment 32b. In the depicted embodiment, the transverse plane 72b corresponds to the central transverse plane 78b. The body portion 84b can also include a plurality of recesses 118b that extend parallel to the superior/inferior coordinate 74b in both the superior and inferior directions relative to the slot axis 116b (FIG. 6).

Herein, the rail portion 82b, rail axis 94b, rail portion cross-section 102b, body portion 84b, elongate slot 112b, slot axis 116b and body portion cross-section 104b of the intermediate modular segment 32b are alternatively referred to as the intermediate rail portion 82b, intermediate rail axis 94b, intermediate rail portion cross-section 102b, intermediate body portion 84b, intermediate elongate slot 112b, intermediate slot axis 116b and intermediate body portion cross-section 104b, to clarify association with the intermediate modular segment 32b.

The intermediate body portion 84b can also be characterized as having a superior lip portion 122b and an inferior lip portion 124b, each being named for their location along the superior/inferior coordinate 74b relative to the transverse plane 72b. The lip portions 122b, 124b are adjacent to and partially define the intermediate elongate slot 112b, and protrude toward each other. A gap 126b is defined between the superior lip portion 122b and the inferior lip portion 124b, defining an open side 128b of the elongate slot 112b. In the depicted embodiment, each lip portion 122b, 124b protrudes toward the central transverse plane 78b. The lip portions 122b and 124b can also define an opposing flanking face 130b that faces in a direction opposite the flanking face 86b of the intermediate body portion 84b.

Referring to FIG. 7 and again to FIG. 6, the opposing end modular segment 32c (C-segment) is depicted in an embodiment of the invention. (It is noted that the cross-section depicted in FIG. 6 applies to both FIGS. 5 and 7). The opposing end modular segment 32c includes a body portion 84c that defines an elongate slot 112c, the elongate slot 112c further defining a slot axis 116c that lies on the transverse plane 72c. The elongate slot 112c includes an interior surface 114c and passes through the body portion 84c of the opposing end modular segment 32c. The body portion 84c includes a body portion cross-section 104c that is normal to the slot axis 116c. The body portion 84c of the opposing end modular segment 32c can also include a superior lip portion 122c and an inferior lip portion 124c having the same characteristics as the superior and inferior lip portions 122b and 124b of the intermediate modular segment 32b. The body portion 84c of the opposing end modular segment 32c can further define a plurality of recesses 118c that are recessed from the interior surface 114c of the elongate slot 112c of the body portion 84c. The recesses 118c can extend radially outward relative to the slot axis 116c and are parallel to the superior/inferior coordinate 74c of the opposing end modular segment 32c.

Herein, the body portion 84c, elongate slot 112c, slot axis 116c and body portion cross-section 104c of the opposing end modular segment 32c are alternatively referred to as the opposing end body portion 84c, opposing end elongate slot 112c, opposing end slot axis 116c and opposing end body portion cross-section 104c, to clarify association with the opposing end modular segment 32c.

The rail heads 92 can each include faces 132 that are substantially planar and substantially parallel to the respective superior/inferior coordinate 74, the faces 132 thereby being at a right angle relative to the respective web portion 88. The body portion 84 of the adjacent, mating modular segment 32, being complementary to the rail portion 82, can include the superior and inferior lip portions 122 and 124 that also include interior faces 134 that are substantially planar and substantially parallel to the superior/inferior coordinate 74 (e.g., FIGS. 5 and 7).

Referring to FIG. 8, an alternative rail cross-section 102d and mating body portion cross section 104d is presented in an embodiment of the invention. For these embodiments, lip portions 122d, 124d also include faces 132d that are each substantially planar, but each being oblique relative to the superior/inferior coordinate 74d so as to define a "dovetail" profile. That is, the planar faces 132d of the rail head 92d that are adjacent the web 88d for the rail portion 82d intersect web 88d at an acute angle θ. The body portion 84d of the adjacent, mating segment, being complementary, also defines an acute angle θ relative the web portion 88d.

Functionally, the right angle or acute angle configurations between the faces 132 and the web portion 88 enhance the mechanical coupling between adjacent segments in a direction that is normal to both the superior/inferior coordinate 74 and rail axis 94. These configurations rely primarily on compressive contact between the engaged segments and less on friction between the segments, thereby providing for a positive mechanical coupling therebetween. The enhanced coupling is particularly advantageous when the segments comprise a soft or compliant material having a relatively low hardness. A non-limiting example of a soft or compliant material is a polymer such a biocompatible polyurethane. A non-limiting example of a hardness of a soft or compliant material is a material with a durometer hardness ranging from about Shore 18 A to about Shore 55D. A further and non-limiting example of a soft or compliant material is a material with a compressive modulus between about 2 and about 100 MPa. In a preferred embodiment, the compressive modulus is between about 6 and about 20 MPa.

The cross-sections 102 and 104 of the various rail portions 82 and the various body portions 84 can be configured to be complementary to itself and the other modular segments 32. That is, the various rail portion cross-sections 102 can be shaped and dimensioned to mate with the various body portion cross-sections 104. Likewise, the various recesses 118 can be positioned and dimensioned to accept (i.e., to be complementary with) the barb portions 96 on the various rail portions 82 of the modular segments 32.

In this way, a given A-segment 32a can be coupled to either a given B-segment 32b or a given C-segment 32c, a given C-segment 32c can be coupled with either a given A-segment 32a or a given B-segment 32b, and a given B-segment 32b can be coupled with another B-segment 32b. The modularity of the system enables the construction of a variety of prosthesis sizes by interlocking the various segments together in a side-by-side manner, the A, B and C-segments 32a, 32b and 32c constituting the building blocks of the modular system.

In certain embodiments, the flanking faces 86 of the various segments are oblique relative to the rail axes 94 (i.e., are not parallel to the rail axes 94). Instead, the flanking faces 86 slope slightly towards the rail axes 94 at an angle α from the proximal end 66 to the distal end 68, as best seen in FIG. 18A. That is, the flanking faces 86 are spaced further from the rail axes 94 at the proximal ends 66 than at the distal ends 68. Thus, for embodiments that include this aspect, the rail axis 94 of a given modular segment 32 will intersect plane of the respective flanking face 86 at a point distal to the modular segment 32.

To accommodate the oblique flanking face configuration, the lip portions 122, 124 of the modular segments 32b and 32c can be of varying thickness from the proximal end 66 to the distal end 68 of the respective body portion 84b, 84c. While the interior face 134 of a given lip portion 122, 124 is parallel to the respective slot axis 116, the thickness of the lip portions 122, 124 (i.e., the dimension normal to the slot axis 116) can decrease from the proximal end 66 to the distal end 68, so that the lip portions 122, 124 themselves form a complementary oblique interface with the oblique flanking face 86 of the adjacent modular segment 32a or 32b.

Referring to FIG. 9, a side view of a modular segment 32a or 32b is presented in an embodiment of the invention. The barb portions 96 can each define an inclined profile 142. The inclined profile 142 intersects an outer surface of the rail portion 82 at an intersection point 144 on the proximal end of the barb portion 96. From the intersection point 144, the dimension of the barb portion increases toward a distal end 146 of the barb portion 96. In the depicted embodiments, the distal ends 146 of the barb portions 96 are parallel to the superior/inferior coordinate 74 of the respective modular segment 32. Thus, in this embodiment, the barb portions 96 each define a right-triangular profile in a plane that is parallel to both the superior/inferior coordinate 74 and the rail axis 94 of a given segment 32a, 32b.

In one embodiment, the corresponding recesses 118 of the body portion 84 of the adjacent modular segment 32b or 32c can define a similar, triangular shape that is complementary to the triangular shape of the barb portion 96 (FIG. 6). In other embodiments, the recesses 118 can be, for example, rectangular, so long as a distal boundary 148 of the recesses 118 are complementary to the distal ends 146 of the barb portions 96.

For assembly of the implant of, for example, FIG. 2b, the B-segment 32b is positioned proximal to the proximal end of the A-segment 32a, so that the slot axis 116b of the body portion 84b of the B-segment 32b is substantially concentric with the rail axis 94a of the rail portion 82a of the A-segment 32a. The body portion 84b of the B-segment 32b is then slid over the rail portion 82a of the A-segment 32a in the distal direction along the rail axis 94a until the barb portions 96a of the rail portion 82a are captured within the recesses 118b of the body portion 84b of the B-segment 32b. The distal end 68b of the body portion 84b of the B-segment 32b can be substantially registered against the stop portion 98a of the A-segment 32a when the barb portions 96a of the A-segment 32a are secured within the recesses 118b of the B-segment 32b.

As the body portion 84b of the B-segment 32b is slid over the rail portion 82a of the A-segment 32a, the interior surface 114b of the elongate slot 112b of the B-segment 32b rides over the protruding barb portions 96a of the A-segment 32a. This interaction causes the barb portions 96a of the A-segment 32a to be compressed and the wall of the body portion of the B-segment 32b to deflect upwards. However, once the barb portions 96a are registered within the respective recess 118b, there is essentially no deformation of the components.

After the B-segment 32b is secured to the A-segment 32a, the C-segment 32c is positioned proximal to the proximal end of the B-segment 32b, so that the slot axis 116c of the body portion of the C-segment 32c is substantially concentric with the rail axis 94b of the B-segment 32b. The body portion 82c of the C-segment 32c is then slid over the rail portion 82b of the B-segment 32b in the distal direction along the rail axis 94b until the barb portions 96b of the rail portion 82b are captured within the recesses 118c of the body portion 84c of the C-segment 32c. The distal end 68c of the body portion 84c of the C-segment 32c can be substantially registered against the stop portion 98b of the B-segment 32b when the barb portions 96b of the B-segment 32b are secured within the recesses 118b of the C-segment 32c.

For a 2-segment implant (FIG. 2A), the C-segment 32c is interlocked directly to the A-segment 32b in similar fashion. Likewise, for an implant having four or more segments, additional intermediate B-segments are interlocked in similar fashion. As a non-limiting example, embodiments can have as many as 8 modular segments (one A-segment 32a, one C-segment 32c, and six B-segments 32b).

Functionally, the various structural aspects of the rail and slot portions 82, 112 of the modular segments 32 prevent relative motion between the modular segments 32 in all directions, even where a relatively soft or compliant material is utilized for the modular segments 32. The engagement of a given rail portion 82 with an adjacent body portion 84 prevents relative motion between the engaged segments along the superior/inferior coordinates 74. Engagement between the barb portions 96 and stop portions 98 of a given modular segment 32, when engaged with an adjacent segment 32, prevent relative motion between the engaged segments 32 along the proximal/distal coordinates 76. Both the lip portions 122 and 124 and the barb portions 96 provide shear resistance to movement parallel to the transverse plane 72. The superior and inferior lip portions 122 and 124 of a given modular segment 32, along with the barb portions 96 of an adjacent, engaged modular segment 32, prevent separation of the modular segments 32.

The inclined profile 142 of the barb portions 96 enable the body portion 84 of an adjacent segment 32 to be more easily slid over the barb portions 96 as the adjacent segment 32 is moved in the distal direction relative to the given segment 32. However, once the barb portions 96 are registered within their corresponding recesses 118, the distal ends 146 of the barb portions 96 interact with the distal boundaries 148 of the recesses 118 to prevent the adjacent segment from moving along the proximal/distal coordinate 76.

For embodiments utilizing oblique flanking faces 86, there is little or no sliding interference between the flanking faces 86 and the superior and inferior lip portions 122 and 124 of adjacent segments until the adjacent segments are at or near the implanted position. This helps limit the frictional load during assembly.

Referring to FIG. 10, a cross-section of a B-segment 32*b* that cuts through the transverse plane 72*b* is presented depicting a mounting port 152*b* in an embodiment of the invention. The modular segments 32 can each include such a mounting port 152 for mounting the respective modular segment 32 to an insertion tool. While the discussion below is directed to the mounting port 152*b*, the general aspects apply to all mounting ports 152.

In one embodiment, the mounting port 152*b* defines a substantially cylindrical cavity 154*b* that is concentric about the rail axis 94*b* of the modular segment 32*b* and is accessible from the proximal end 66*b* of the modular segment 32*b*. The mounting port 152*b* can further include internal detents 156 that extend from one side of an internal wall 158*b* of the mounting port 152*b*. In one embodiment, the detents 156 can each define a triangular or right triangular profile 162, wherein a proximal face 164 of each detent 156 is inclined relative to the rail axis 94*b* and a distal face 166 of the detent 156 is orthogonal to or only slightly acute relative to the rail axis 94*b*.

Referring to FIGS. 11, 11A and 11B, the A/B insertion tool 36*a*, used to augment insertion of both the A- and B-modular segments 32*a* and 32*b* is depicted in an embodiment of the invention. The A/B insertion tool 36*a* includes a shaft portion 172*a* with a flag 174*a* extending from a proximal end 176*a* and a tip portion 178*a* extending from a distal end 182*a*. The tip portion 178*a* defines a rotation axis 184*a* and further defines notches 186 formed on one side that are shaped and positioned complementary to the detents 156 of the mounting ports 152. In certain embodiments, the shaft portion 172*a* includes a cross-section 188*a* that has the same profile as the rail head 92 of the modular segments 32. Accordingly, when in the proper rotational orientation about the rotation axis 184*a*, the shaft portion 172*a* effectively provides a proximal extension of the rail head 92. In the depicted embodiment, the shaft portion 172*a* of the A/B insertion tool 36*a* defines a "D-shaped" profile 190*a* having an arcuate portion 192*a* and a flat face portion 194*a*. The flag 174*a* of the A/B insertion tool 36*a* can be "L-shaped" as depicted in FIG. 11, with a short leg 196*a* of the flag 174*a* extending from the flat face portion 194*a* of the D-shaped shaft portion 172*a*.

Referring to FIGS. 12 and 12A, assembly of the A/B insertion tool 36*a* and one of the A- and B-segments 32*a* and 32*b* is depicted in an embodiment of the invention. In one embodiment, the assembly can be augmented by a segment loading platform 200. In one embodiment, the segment loading platform 200 includes a segment bay 202 that is aligned with a "U-shaped" channel 204 having an arcuate portion 206 concentric about a loading axis 208. The segment bay 202 is configured with a bottom portion 212 configured to accept and register the rail portion of the modular segment 32*a* or 32*b*. The U-shaped channel 204 is dimensioned for sliding engagement with the D-shaped profile 190*a* of the shaft portion 172*a*.

One of the A- or B-segments 32*a* or 32*b* is placed in the segment bay 202 so that the rail portion 82 of the segment 32 is properly registered within the bottom portion of the segment bay. The shaft portion 172*a* of the A/B insertion tool 36*a* is placed within the U-shaped channel 204 of the segment loading platform 200 so that the arcuate portion 192*a* of the D-shaped profile 190*a* registers against the arcuate portion 206 of the U-shaped channel 204. The registrations of the modular segment 32*a* or 32*b* and the shaft portion 172*a* of the A/B insertion tool 36*a* aligns the rotation axis 184*a* of the tip portion 178*a* and the rail axis 94*a* (and therefore the mounting port 152*a* or 152*b*) of the corresponding modular segment 32*a* or 32*b*. The registrations also rotationally orient the tip portion 178*a* of the A/B insertion tool 36*a* and the mounting port 152*a* or 152*b* of the modular segment 32*a* or 32*b* so that the notches of the tip portion 178*a* are aligned with the detents 156*a* or 156*b* of the mounting port 152*a* or 152*b*. The tip portion 178*a* is slid into the mounting port 152*a* or 152*b* until each of the plurality of detents 156*a* or 156*b* of the mounting port 152*a* or 152*b* occupies a corresponding one of the notches 186*a* on the tip portion 178*a*.

It is noted that the C-segment 32*c* does not include a mounting rail, and therefore cannot include a mounting port that is concentric with a rail portion. Accordingly, the C-segment includes a mounting port 152*c* formed in the body portion 84*c*, the mounting port 152*c* defining an axis 214 that is parallel with and on the same transverse plane 72*c* as the slot axis 116*c* and having the same aspects as the mounting ports 152*a* and 152*b* of the A- and B-segments 32*a* and 32*b*.

Referring to FIGS. 13A through 13H, an assembly sequence is depicted for the three-segment prosthesis 34*b* of FIG. 2B. An A-segment/insertion tool assembly 220*a* comprising the A-segment 32*a* and the A/B insertion tool 36*a* is first placed in an evacuated disc nucleus space (FIG. 13A; evacuated disc nucleus space not depicted). A B-segment/insertion tool assembly 220*b* comprising the B-segment 32*b* and another A/B insertion tool 36*b* is then slid over a proximal end 222*a* of the A-segment/insertion tool assembly 220*a* and translated along the shaft 172*a* of the A/B insertion tool 36*a* of the A-segment/insertion tool assembly 220*a* (FIG. 13B). During this step, the open side 128*b* of the elongate slot 112*b* of the B-segment 32*b* is aligned to pass over the short leg 196*a* of the L-shaped flag 174*a* of the A-segment insertion tool 36*a* of the A-segment/insertion tool assembly 220*a*, which also places the elongate slot 112*b* of the B-segment 32*b* in proper orientation for translation along the D-shaped shaft 172*a* of the A/B insertion tool 36*b* of the B-segment/insertion tool assembly 220*b*.

The B-segment 32*b* is then slid over the rail portion 82*a* of the A-segment 32*a* until the B-segment 32*b* registers against the stop portion 98*a* of the A-segment 32*a* (FIG. 13C). The open side 128*b* of the elongate slot 112*b* slides over the web 88*b* of the rail portion 82*b*, the open side 128*b* having been properly aligned when slid over the short leg 196*a* of the L-shaped flag 174*a*. The user can determine that the B-segment 32*b* is in place when the flags 174*a* and 174*b* of the A/B insertion tools 36*a* and 36*b* of the A- and B-segment insertion tool assemblies 220*a* and 220*b* are aligned. Upon registration of the B-segment 32*b* against the stop portion 98*a* of the A-segment 32*a*, the barb portions 96*a* on the rail portion 82*a* of the A-segment 32*a* should be registered within the recesses 118*b* of the B-segment 32*b*. However, the user can tug the B-segment/insertion tool assembly 220*b* in the proximal direction relative to the A-segment/insertion tool assembly 220*a* to assure that the barb portions 96*a* are set within the recesses 118*b*.

The A/B insertion tool 36*a* of the A-segment/insertion tool assembly 220*a* is then removed. Removal is accomplished by rotation the A/B insertion tool 36a of the A-segment/insertion tool assembly 220a 180° about the rotation axis 184a (FIG. 13D). This action causes the notches 186a of the tip portion 178a of the A/B insertion tool 36a of the A-segment/insertion tool assembly 220a to rotate away from the detents 156a in the mounting port of the A-segment 32a, thus enabling the A/B insertion tool 36a of the A-segment/insertion tool assembly 220a to be removed from the mounting port 156a with reduced interference from the detents 156a. The A/B insertion tool 36a of the A-segment/insertion tool assembly 220a is then removed from the mounting port 152a, leaving only the A- and B-segments 32a and 32b coupled to the B-segment/insertion tool assembly 220b (FIG. 13E).

A C-segment/insertion tool assembly 220c comprising the C-segment 32c and the C insertion tool 36c is then aligned so that the slot portion 112c of the C-segment 32c is slid over a proximal end 222b of the B-segment/insertion tool assembly 220b, and the C-segment/insertion tool assembly 220b being translated along the shaft 172b of the insertion tool 36b of the B-segment/insertion tool assembly 220b (FIG. 13F). The C insertion tool 36c is described in more detail below in the discussion attendant to FIG. 19. The C-segment 32c is then slid over the rail portion 82b of the B-segment 32b until the C-segment 32c registers against the stop portion 98b of the B-segment 32b (FIG. 13G). The insertion tool 36b of the B-segment/insertion tool assembly 220b is then removed (FIG. 13H). The steps depicted at FIGS. 13F through 13H are conducted in the same manner as the steps depicted at FIGS. 13B through 13E.

The insertion tool of the C-segment/insertion tool 36c is removed by rotating the insertion tool 36c 180° (FIG. 13H) and removing it from the mounting port 152c, thereby leaving the prosthesis fully assembled an in place (FIG. 2B).

In certain embodiments, supplemental tools can be included and utilized in for enhanced manipulation of the modular segments. The supplemental tools are of particular utility when handling modular segments that are of a homogeneous, compliant material. The supplemental tools can include the removal tool 44, the A-segment stabilizer 46, the B-segment stabilizer 48 and the C-segment stabilizer 52 (FIG. 1).

Referring to FIGS. 14 and 14A, the removal tool 44 is depicted in an embodiment of the invention. The removal tool 44 includes a handle portion 232 and a shaft portion 234. The shaft portion 234 defines a bore 236 having an inner diameter 238 concentric about a central axis 242. The inner diameter 238 of the bore 236 is dimensioned large enough to slide over the D-shaped profile 190a or 190b of the A- and B-segment insertion tool 36a or 36b, as well as the round profile of the C-segment insertion tool 36c. The removal tool 44 includes a slot 244 on one side thereof, the slot 244 extending on one side of the removal tool and from a location 246 proximate a proximal end 248 of the removal tool 44 through a distal end 252 of the removal tool 44.

Referring to FIGS. 15A through 15D, operation of the removal tool 44 is depicted in an embodiment of the invention. Typically after the insertion tool has been rotated 180° to disengage the detents 156 and notches 186 (FIGS. 15A and 15B), the central axis 242 of the removal tool 44 is aligned with the rotation axis 184 of the insertion tool 36 and slid over the proximal end 176 of the insertion tool 36, the slot 244 being aligned to pass over the short leg 196 of the L-shaped flag 174. The shaft portion 234 of the removal tool 44 is slid over the shaft portion 172 of the insertion tool 36 until the distal end 252 of the removal tool 44 is brought into contact with the modular segment 32 (FIG. 15C). The insertion tool 44 is then pulled out of the mounting port 152 by application of a clamping force F between the flag portion 174 of the insertion tool 36 and the handle portion 232 of the removal tool 44 (FIG. 15D). The operator typically applies the clamping force F by squeezing the flag portion 174 and the handle portion 232 between the index finger and the thumb or palm of the hand.

Functionally, while the act of rotating a given insertion tool 36 180° makes removal of the insertion tool 36 from the mounting port 152 easier, the friction between the tip portion 178 of the insertion tool 36 and the modular segment 32 can still be substantial, in part because the detents 156 are compressed against the cylindrical surface of the tip portion 178 after the 180° rotation. The removal tool 44 provides a controlled, mechanically leveraged way to remove insertion tools 36 in situ while maintaining a low profile.

Referring to FIGS. 16, 16A, 17, 17A and 17B, the A- and B-segment stabilizers 46 and 48 are depicted in embodiments of the invention. The A- and B-segment stabilizers 46 and 48 include many common aspects, which are indicated in the figures with like-numbered numerical references. The A-stabilizer 46 includes a shaft portion 262 having a handle 264 attached at a proximal end 266. The shaft portion 262 includes what is effectively a channel structure 268 defining a channel 272 on one side thereof, the channel structure 268 including opposed flanges 274 and 276 separated by a flat portion 278. The channel 272 thus defined is dimensioned to enable insertion tools 36 to slidably translate therein, with the flat portion 278 of the D-shaped shaft 172 engaged with the flat portion 278 of the A-segment stabilizer 46. At a distal end 282, the flat portion 278 includes an extension portion 284 that extends beyond the opposed flanges 274, 276, the extension portion 284 including a slot 286 formed thereon. The slot 286 is formed along an elongate axis 292 and is accessible from the distal end 282.

The B-segment stabilizer 48 also includes the channel structure 268 extending from the proximal end 266 to near the distal end 282. At the proximal end 266, the B-segment stabilizer includes a ramp portion 294 formed within the channel 272. In the absence of a handle, the B-segment stabilizer includes a grip portion 296 formed on the proximal end 266. Near the distal end 282, the B-segment stabilizer 48 includes an additional guide structure 302 that effectively defines an asymmetric H-beam profile 304. The channel structure 272 and guide 302 structure define the channel 272 continuously along the length of the B-segment stabilizer 48. The guide structure 302 includes opposed flanges 274 and 276 that extend normal to the flat portion 278 in both directions. The guide structure 302 also includes opposed lip portions 306 that extend toward each other to define a gap 308 therebetween.

Referring to FIGS. 18A and 18B, operation of the A-segment stabilizer 46 is depicted in an embodiment of the invention. Prior to insertion of the A-segment 32a into the evacuated disc nucleus space, the A-segment/insertion tool assembly 220a is loaded into the channel 272 of the A-segment stabilizer 46 (FIG. 18A). After or simultaneously with the loading, the A-segment stabilizer 46 is translated toward the A-segment 32a until the web 88a of the rail portion 82a registers within the slot 286 (FIG. 18B).

For the B-segment stabilizer 48, the guide structure 302 is slid over the distal end 176a of the A insertion tool 36a to capture the D-shaped shaft portion 172a of the A insertion tool 36a (shown in phantom in FIG. 17A) between the flange portions 274, 276 and lip portions 306 of the guide structure 302 of the B-segment stabilizer 48. The channel 272 of the B-segment stabilizer 48 is translated over the B-segment/ insertion tool assembly 220b until the web 88b of the rail portion 82b is registered in the slot 286. In the depicted embodiment, the B-segment stabilizer 48 does not include a handle akin to the A-segment stabilizer 46 because such a handle would create clutter and interference amongst the flags 178a and 178b of the A- and B-insertion tools 36a and 36b. In this way, additional guidance and control for coupling the B-segment 32b to the A-segment 32a is provided in situ.

The ramp portion 294 guides the flags 174a and 174b at the proximal ends of the insertion tools 36a and 36b away from each other during assembly of the prosthesis 34. This prevents the flag 174b of the A/B insertion tool 36B from catching on the flag 174a of the adjacent A/B insertion tool 36a.

Removal of the A- and B-segment stabilizers 46 and 48 is accomplished by disengaging them from the web 88a, 88b of the respective rail portion 82a, 82b in the proximal direction.

Referring to FIGS. 19, 19A and 19B (referred to collectively as FIG. 19), the C insertion tool 36c is depicted in an embodiment of the invention. The C insertion tool 36c includes a shaft portion 172c having a tip portion 178c at a distal end 182c and a flag portion 174c at a proximal end 176c. In one embodiment, the flag portion 174c extends in an opposite direction from the flag portions 174a, 174b of the A/B insertion tools 36a, 36b. The tip portion 178c defines a tip portion axis 310. The notch aspects 186c of the tip portion 178c for the C insertion tool 36c can the same as for the A/B insertion tool 36a. The shaft portion 172c of the C insertion tool 36c is essentially cylindrical about a cylindrical axis 312. In the depicted embodiment, the cylindrical axis 312 of the shaft portion 172c and the tip portion axis 310 of the tip portion 178c are eccentric (FIGS. 19A and 19B).

Referring to FIGS. 20, 20A and 20B, the C-segment stabilizer 52 is depicted in an embodiment of the invention. The C-segment stabilizer 52 includes a hollow shaft portion 322 having a handle 324 on a proximal end 326 and an guide structure 328 near a distal end 332. The hollow shaft portion 322 includes structure defining a slot 334 extending on a first side 336 of thereof and from a location 338 proximate the proximal end 326 and through the distal end 332 of the C-segment stabilizer 52. The guide structure 328 comprises two opposing flanges 342 and 344 that extend from a second side 346 of the hollow shaft portion 322, the second side 346 being opposite the first side 336. The opposing flanges 342, 344 each include lip portions 352 that extend toward each other to define a gap 356 therebetween. The A/B insertion tool 36b and the C insertion tool 36c are depicted in phantom in FIG. 20B.

In operation, the hollow shaft portion 322 of the C-segment stabilizer 52 is aligned with the cylindrical axis 312 of the C insertion tool 36c and with the slot 334 aligned to pass over the flag portion 174c. The C-segment stabilizer 52 is then translated over the C insertion tool 36c until the distal end 332 engages the C-segment 32c.

Functionally, the guide structure 328 captures the D-shaped shaft 172c of the adjacent A/B insertion tool 36b between the flanges 324 and 344 of the guide structure 328, to further assist the user in guiding the B-segment 32b into the evacuated disc nucleus space. The slot 334 of the C-segment stabilizer enables passage of the hollow shaft portion 322 over the shaft flag portion 174c of the C insertion tool 36c. Likewise, the gap 356 enables passage of the guide structure 328 over the flag portion 174b of the A/B insertion tool 36b. The inner diameter of the hollow shaft 322 is dimensioned so that the A/B insertion tool 36b cannot be inserted in the C-segment stabilizer. Thus, the round hollow shaft 322 of the C-segment stabilizer 52 serves as a key to prevent insertion of the A/B insertion tool 36a therein. The eccentricity of the tip portion 178c relative to the shaft portion 172c allows room for the structure of the hollow shaft portion 322 between the insertion tools 36b and 36c. The distal end 332 of the C-segment stabilizer 52 provides a bearing surface that spreads the force of the insertion operation over a larger area, thus preventing deformation of the C-segment 32c during insertion of the C-segment 32c.

A purpose of the A-, B-, and C-segment stabilizers 46, 48 and 52 generally is to enable manipulation the respective A-, B- and C-segments 32a, 32b and 32c during implantation, as well as maneuvering the prosthesis 34 within the evacuated disc nucleus space while the prosthesis 34 is at various stages of assembly. The stabilizers 46, 48, 52 reduce the risk of the tip portion 178 of the various insertion tools 36 becoming dislodged from the respective mounting port 152 during positioning of the partially or fully assembled prosthesis 34.

In certain embodiments, various of the components discussed above are included as a kit. The kit can include some or all of the components presented in FIG. 1. The kit can also include operating instructions on a tangible medium such as a paper document, a compact disc (CD), a digital video disc (DVD), or a central computer accessed, for example, over the internet. The operating instructions can include various of the instructions and sequences described above.

What is claimed is:

1. A modular disc nucleus prosthesis adapted for implantation in an evacuated disc nucleus space, the prosthesis comprising:
   a plurality of modular segments wherein each modular segment is formed of a single, soft compliant material, wherein the compressive modulus and shore hardness are uniform through the plurality of modular segments, each modular segment including a superior side, an inferior side, a proximal end, and a distal end opposite the proximal end, the superior and inferior sides being disposed on opposing faces of a transverse plane of the respective modular segment with said superior and inferior sides configured to contact the periphery of the evacuated disc nucleus space with the single, soft compliant material, said transverse plane being orthogonal to a superior/inferior coordinate of the respective modular segment when in an implanted configuration, each of said plurality of modular segments being adapted to interlock with an adjacent one of said plurality of modular segments in a side-by-side arrangement on said transverse plane when in said implanted configuration,
   said plurality of modular segments including:
   a first end modular segment including a first end body portion and a first end rail portion, said first end body portion configured to contact the periphery of the evacuated disc nucleus space with the single, soft compliant material, said first end rail portion extending from a flanking face of said first end body portion said first end rail portion defining a first end rail axis that passes through the proximal end and the distal end of said first end modular segment, said first end rail axis lying on said transverse plane of said first end modular segment, said first end rail portion including a plurality of diametrically opposed barbs that extend radially outward relative to said first end rail axis and parallel to the superior/inferior coordinate of said first end modular segment, said first end rail portion having a first end rail cross-section that is normal to said first end rail axis, wherein said first end rail portion includes a web and a rail head, said web being disposed between said rail head and said flanking face and extending along said transverse plane, wherein said rail head includes planar faces that intersect said web at one of a right angle and an acute angle;

an opposing end modular segment including an opposing end body portion and an opposing end elongate slot having an interior surface, said opposing end body portion configured to contact the periphery of the evacuated disc nucleus space with the single, soft compliant material, said opposing end elongate slot passing through said body portion of said opposing end modular segment to define an opposing end slot axis, said opposing end slot axis lying on a transverse plane that is normal to the superior/inferior coordinate of said opposing end modular segment, said body portion of said opposing end modular segment defining an opposing end body cross-section normal to said opposing end slot axis, said body portion of said opposing end modular segment further defining a plurality of recesses that are recessed from said interior surface of said opposing end elongate slot, each of said plurality of recesses extending radially outward relative to said opposing end slot axis and parallel to the superior/inferior coordinate of said opposing end modular segment, wherein said body portion of said opposing end modular segment includes a superior lip portion and an inferior lip portion, each of the lip portions being adjacent said opposing end elongate slot and extending parallel to said first end flanking face and each protruding toward said transverse plane of said opposing end modular segment, each of said superior lip portion and said inferior lip portion of said opposing end modular segment defining an interior face that complements said planar faces of said rail head, wherein said diametrically opposed barbs and said plurality of recesses are defined by the single, soft compliant material such that the diametrically opposed barbs are adapted for capture and retention within said plurality of recesses with said single, soft compliant material facilitating affirmative interlocking when in an implanted configuration.

2. The prosthesis of claim 1, wherein:

said opposing end body cross-section is complementary to said first end rail cross-section of said first end rail portion for sliding engagement between said first end modular segment and said opposing end modular segment along said first end rail axis;

each of said plurality of recesses of said opposing end modular segment is positioned and dimensioned complementary to a corresponding one of said plurality of barbs of said first end modular segment; and said first end modular segment and said opposing end modular segment are adapted to interlock with each other to define an implanted configuration presenting a substantially continuous periphery that generally corresponds to said evacuated nucleus disc space.

3. The prosthesis of claim 1, said plurality of modular segments including:

an intermediate modular segment including an intermediate body portion and an intermediate rail portion, said intermediate body portion defining an intermediate superior side and an intermediate inferior side, said intermediate superior and intermediate inferior sides configured to contact the periphery of the evacuated disc nucleus space with the single, soft compliant material, said intermediate rail portion extending from a flanking face of said intermediate body portion, said intermediate rail portion defining an intermediate rail axis that passes through the proximal end and the distal end of said intermediate modular segment, said intermediate rail portion including a plurality of diametrically opposed barbs that extend radially outward relative to said intermediate rail axis and parallel to the superior/inferior coordinate of said intermediate modular segment, said intermediate rail portion having an intermediate cross-section normal to said intermediate rail axis, wherein said intermediate body portion defines an intermediate elongate slot having an interior surface, said intermediate elongate slot passing through said intermediate body portion to define an intermediate slot axis, said intermediate rail axis and said intermediate slot axis being substantially parallel to each other and lying on the transverse plane of said intermediate modular segment, said intermediate body portion defining an intermediate body cross-section normal to said intermediate slot axis, said body portion of said intermediate modular segment further defining a plurality of recesses that are recessed from said interior surface of said intermediate elongate slot and extend radially outward relative to said intermediate slot axis and parallel to the superior/inferior coordinate of said intermediate modular segment, said intermediate body portion including a superior lip portion and an inferior lip portion, each being adjacent said intermediate elongate slot and extending parallel to said first end flanking face and each protruding toward said transverse plane of said intermediate modular segment wherein said diametrically opposed barbs and said plurality of recesses of the intermediate body portion are defined by the single, soft compliant material.

4. The prosthesis of claim 3, wherein:

said intermediate body cross-section is complementary to said first end rail cross-section of said first end rail portion for sliding engagement between said first end modular segment and said intermediate modular segment along said first end rail axis, each of said plurality of recesses of said intermediate modular segment being positioned and dimensioned complementary to a corresponding one of said plurality of diametrically opposed barbs of said first end modular segment, said diametrically opposed barbs of said first end rail portion being configured for capture within said plurality of recesses of said intermediate modular segment when in the implanted configuration; and said opposing end body cross-section is complementary to said intermediate rail cross-section for sliding engagement between said opposing end modular segment and said intermediate modular segment along said intermediate rail axis, each of said plurality of recesses of said opposing end modular segment being positioned and dimensioned complementary to a corresponding one of said plurality of diametrically opposed barbs of said intermediate modular segment, said diametrically opposed barbs of said intermediate rail portion being adapted for capture within said plurality of recesses of said body portion of said opposing end modular segment when in the implanted configuration; and said first end modular segment being adapted to interlock with said intermediate modular segment and said intermediate modular segment being adapted to interlock with said opposing end modular segment to define an implanted configuration presenting a generally continuous periphery of the single, soft compliant material that generally corresponds to said evacuated nucleus disc space.

5. The prosthesis of claim 3, wherein each of said plurality of modular segments includes structure defining a mounting port disposed on and accessible from said proximal end, said mounting port including an interior surface and a plurality of detents that extend from a first side of said interior surface, wherein a second side opposite said first side defines a cylindrical surface.

6. A system for configuring the modular disc nucleus prosthesis of claim 5, the system comprising:

a plurality of insertion tools, one for each of said plurality of segments and each including a tip portion having a plurality of notches formed on one side thereof, said tip portion extending along a rotation axis and being dimensioned for insertion into said mounting ports of said modular segments, said notches being configured to mate with said detents within said mounting port, wherein said tip portion is selectively releasable from the corresponding one of said mounting ports by rotating said insertion tool approximately 180 degrees about said central axis.

7. The prosthesis of claim 1, wherein single, soft compliant material has a compressive modulus between about 6 and about 20 MPa.

8. The prosthesis of claim 1, wherein said first end segment further comprises a stop portion at the distal end of said first end segment.

9. The prosthesis of claim 1, wherein said first end rail portion defines a first mounting port accessible from the proximal end of said first end modular segment.

10. The prosthesis of claim 1, wherein the transverse plane corresponds to a central transverse plane.

* * * * *